US010206955B2

(12) United States Patent
Yoon et al.

(10) Patent No.: US 10,206,955 B2
(45) Date of Patent: Feb. 19, 2019

(54) COMPOSITIONS OF ASCORBIC ACID AND BONE MORPHOGENETIC PROTEIN 4 (BMP-4) FOR CELL GROWTH AND USES RELATED THEREO

(71) Applicant: EMORY UNIVERSITY, Atlanta, GA (US)

(72) Inventors: Young-Sup Yoon, Atlanta, GA (US); Jaeyeaon Cho, Decatur, GA (US)

(73) Assignee: Emory University, Atlanta, GA (US)

( * ) Notice: Subject to any disclaimer, the term of this patent is extended or adjusted under 35 U.S.C. 154(b) by 310 days.

(21) Appl. No.: 14/933,052

(22) Filed: Nov. 5, 2015

(65) Prior Publication Data
US 2016/0166616 A1    Jun. 16, 2016

Related U.S. Application Data

(60) Provisional application No. 62/075,419, filed on Nov. 5, 2014.

(51) Int. Cl.
A61K 35/33     (2015.01)
C12N 15/113    (2010.01)
A61K 38/18     (2006.01)
A61K 31/375    (2006.01)
C12N 5/077     (2010.01)

(52) U.S. Cl.
CPC .......... A61K 35/33 (2013.01); A61K 31/375 (2013.01); A61K 38/1875 (2013.01); C12N 5/0657 (2013.01); C12N 15/113 (2013.01); C12N 2310/141 (2013.01); C12N 2320/31 (2013.01); C12N 2500/38 (2013.01); C12N 2501/155 (2013.01); C12N 2501/65 (2013.01); C12N 2506/1307 (2013.01)

(58) Field of Classification Search
CPC .............. A61K 31/375; A61K 38/1875; C12N 15/113; C12N 2320/31
See application file for complete search history.

(56) References Cited

U.S. PATENT DOCUMENTS

2014/0011281 A1   1/2014 Dzau

FOREIGN PATENT DOCUMENTS

WO    2009092005    7/2009
WO    2011023413    3/2011
WO    2011154553   12/2011

OTHER PUBLICATIONS

Cao et al. Ascorbic acid enhances the cardiac differentiation of induced pluripotent stem cells through promoting the proliferation of cardiac progenitor cells, Cell Research (2012) 22:219-236.
Chang et al. Mesenchymal Stem Cell-Like Properties in Fibroblasts, Cell Physiol Biochem 2014, 34:703-714.
Chen et al. Inefficient Reprogramming of Fibroblasts into Cardiomyocytes Using Gata4, Mef2c, and Tbx5, Circ Res. 2012, 111:50-55.
Cho et al. Non-viral Direct Reprogramming of Fibroblasts Into a Three Dimensional Vascularized Cardiomimetic Tissue, Circulation. 2014, 130:A15412.
Cordes et al. MicroRNA Regulation of Cardiovascular Development, Circ Res. 2009, 104(6): 724-732.
Ieda et al. Direct Reprogramming of Fibroblasts into Functional Cardiomyocytes by Defined Factors, Cell 142, 375-386, 2010.
Jayawardena et al. MicroRNA-Mediated In Vitro and In Vivo Direct Reprogramming of Cardiac Fibroblasts to Cardiomyocytes, Circ Res. 2012, 110:1465-1473.
Qian et al. In vivo reprogramming of murine cardiac fibroblasts into induced cardiomyocytes, Nature 485, 593-598, 2012.
Song et al. Heart repair by reprogramming non-myocytes with cardiac transcription factors, Nature. 2012, 485(7400):599-604.
Sun et al. Bone Morphogenetic Protein-4 Mediates Cardiac Hypertrophy, Apoptosis, and Fibrosis in Experimentally Pathological Cardiac Hypertrophy, Hypertension. 2013, 61:352-360.
Talluri et al. Non-viral reprogramming of fibroblasts into induced pluripotent stem cells by Sleeping Beauty and piggyBac transposons, Biochemical and Biophysical Research Communications, 450 (2014) 581-587.
Chen et al. Fibroblasts in post-infarction infammation and cardiac repair. Biochemica et Biophysica Acta 1833 (2013) 945-53.

Primary Examiner — J. E. Angell
(74) Attorney, Agent, or Firm — Emory Patent Group

(57) ABSTRACT

This disclosure relates to compositions comprising ascorbic acid and bone morphogenetic protein 4 (BMP-4) for growing cells and making tissues. In certain embodiments, this disclosure relates to methods of creating cardio-mimetic tissues (CMTs) by culturing the cells in the presence of ascorbic acid and bone morphogenetic protein 4 and optionally inserting into cells a muscle specific microRNA or related nucleobase polymer and under conditions such that a cardio-mimetic tissue is formed that is capable of spontaneously contracting.

14 Claims, 9 Drawing Sheets
Specification includes a Sequence Listing.

COMPOSITIONS OF ASCORBIC ACID AND BONE MORPHOGENETIC PROTEIN 4 (BMP-4) FOR CELL GROWTH AND USES RELATED THEREO

CROSS-REFERENCE TO RELATED APPLICATIONS

This application claims the benefit of priority to U.S. Provisional Application No. 62/075,419 filed Nov. 5, 2014. The entirety of this application is hereby incorporated by reference for all purposes.

STATEMENT REGARDING FEDERALLY FUNDED RESEARCH

This invention was made with government support under 1DP3DK094346 awarded by NIDDK, and HHSN268201000043C and R01 HL127759 awarded by NHLBI. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 14150US-updated_ST25.txt. The text file is 25 KB, was created on Dec. 27, 2017, and is being submitted electronically via EFS-Web.

BACKGROUND

After injury, human postnatal hearts do not recover appropriately because cardiomyocytes (CM) have a limited proliferation capacity. Accordingly, cell therapy has emerged as a new option for regenerating damaged myocardium. Although various stem or progenitor cells are reported as effective, obstacles include low efficiency for generating pure cardiomyocytes, low cell retention after being transplanted into the heart, immunologic incompatibility, and tumor formation. Thus, there is a need to find improved methods of treating heart injury.

Attempts have been made to directly reprogram somatic cells into CM-like cells using specific cardiac transcription factors (TFs) or miRNAs. Ieda et al. report reprogramming of fibroblasts into functional cardiomyocytes. Cell, 2010, 142:375-386. Qian et al. report in vivo reprogramming of murine cardiac fibroblasts into induced cardiomyocytes. Nature, 2012, 485:593-598. Song et al. report heart repair by reprogramming non-myocytes with cardiac transcription factors. Nature, 2012, 485:599-604. Chen et al. report inefficient reprogramming of fibroblasts into cardiomyocytes using gata4, mef2c, and tbx5. Circulation research, 2012, 111:50-55.

Jayawardena et al. report microRNA-mediated in vitro and in vivo direct reprogramming of cardiac fibroblasts to cardiomyocytes. Circulation research, 2012, 110:1465-1473.

Cao et al. report ascorbic acid enhances the cardiac differentiation of induced pluripotent stem cells through promoting the proliferation of cardiac progenitor cells. Cell Research, 2012, 22:219-236.

Sun et al. report bone morphogenetic protein-4 mediates cardiac hypertrophy, apoptosis, and fibrosis in experimentally pathological cardiac hypertrophy. Hypertension, 2013, 61(2):352-60.

Chang & Guo report mesenchymal stem cell-like properties in fibroblasts. Cell Physiol Biochem, 2014, 34(3):703-14.

References cited herein are not an admission of prior art.

SUMMARY

This disclosure relates to compositions comprising ascorbic acid and bone morphogenetic protein 4 (BMP-4) for growing cells. In certain embodiments, this disclosure relates to methods of creating cardio-mimetic tissues (CMTs) by culturing the cells in the presence of ascorbic acid and bone morphogenetic protein 4 and optionally inserting into cells a muscle specific microRNA or related nucleobase polymer and under conditions such that a cardio-mimetic tissue is formed that is capable of spontaneously contracting.

In additional embodiments, the disclosure contemplates the use of a combination of ascorbic acid and bone morphogenetic protein 4 (BMP-4) for making a variety of tissues by applying a tissue specific microRNA within a cell, e.g., stem, precursor cells or any somatic cells, in order induce development of specific tissues.

In certain embodiments, the disclosure relates to methods of making cardio-mimetic tissue by mixing cells with ascorbic acid and bone morphogenetic protein 4, optionally in combination, and inserting into the cells a nucleobase polymer with a nucleotide sequence consisting of or comprising a sequence selected from AUAAGAC-GAACAAAAGGUUUGU (SEQ ID NO: 1) or variants thereof wherein each U is individually and independently uracil or thymine and under conditions such that a tissue is formed that is capable of spontaneously contracting.

In certain embodiments, the cells are fibroblasts, human dermal fibroblasts, human somatic cells, human blood cells, human cells with pluripotency or induce pluripotency, human CD31 or CD34 cells derived from bone marrow or peripheral blood, human urine-derived cells, and human urine-derived mesenchymal cells.

In certain embodiments, inserting the nucleobase polymer is done by mixing the nucleobase polymer in the presence or complex with a cationic lipid and exposing the mixture to a cell or by incorporating the nucleotide sequence in a viral nucleic acid or particle, plasmid, or other vector.

In certain embodiments, the cardio-mimetic tissue comprises cells that have an increased expression of mRNA Myh6 when compared to cells mixed with ascorbic acid and bone morphogenetic protein 4 in the absence of the nucleobase polymer.

In certain embodiments, the cardio-mimetic tissue comprises cells have increased expression of TNNT2 when compared to cells mixed with ascorbic acid and bone morphogenetic protein 4 in the absence of the nucleobase polymer.

In certain embodiments, the variant of SEQ ID NO: 1 has greater than 65, 70, 75, 80, 85, 90, or 95% sequence identity to SEQ ID NO: 1

In certain embodiments, SEQ ID NO: 1 or the variant of SEQ ID NO: 1 has one, two, three, four, five, six, or seven nucleotide substitutions, deletions, insertions, or combinations thereof.

In certain embodiments, the variant of SEQ ID NO: 1 comprises the sequence UAAGACXXXCA(X)$_n$AXGCUU (SEQ ID NO: 2) wherein n is 2 or 3, U is individually and independently uracil or thymine, and X is individually at each occurrence any nucleotide.

In certain embodiments, the disclosure relates to methods of treating heart disease comprising, isolating cells from a subject diagnosed with heart disease providing isolated cells; making cardio-mimetic tissue capable of spontaneously contracting by the process of mixing the isolated cells with ascorbic acid and bone morphogenetic protein 4, and optionally, inserting or expressing inside the isolated cells a nucleobase polymer comprising a nucleotide sequence consisting of or comprising AUAAGAC-GAACAAAAGGUUUGU (SEQ ID NO: 1) or variants thereof wherein U is individually and independently uracil or thymine, and wherein the process is done under conditions such that a tissue capable of spontaneously contracting is formed providing a cardio-mimetic tissue; and implanting the cardio-mimetic tissue effectively on or in the heart of the subject.

In certain embodiments, the disclosure relates to non-naturally occurring nucleobase polymers comprising or consisting essentially of a nucleotide sequence selected from: SEQ ID NO: 1-134 or variant thereof. In certain embodiments, non-naturally occurring nucleobase polymer is non-naturally occurring because it contains at least one sugar modification, phosphate modification, nucleotide base modification.

In certain embodiments, the disclosure relates to methods of treating heart disease or other vascular condition comprising administering an effective amount of ascorbic acid or derivative thereof and bone morphogenetic protein 4 optionally in combination with a nucleobase polymer comprising sequence SEQ ID NO: 1 or variants thereof to a subject in need thereof. In certain embodiments, the subject is a human, wherein bone morphogenetic protein 4 is a human isoform, wherein the administration is oral, by injection into the blood, peritoneal cavity, or a heart muscle, and wherein the subject is diagnosed with having had a myocardial infarction or other vascular disease.

DETAILED DISCUSSION

Figure 1A:
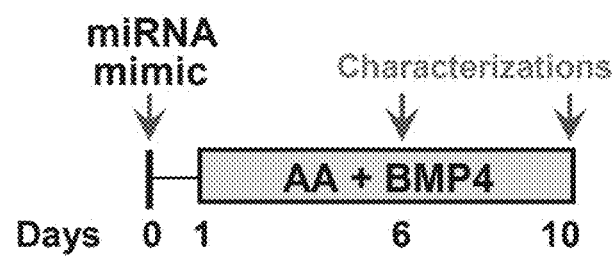
FIG. 1A shows a scheme for reprogramming mouse fibroblast cells (MTTFs) into cardio-mimetic tissue (CMT).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

In this specification and in the claims that follow, reference will be made to a number of terms that shall be defined to have the following meanings unless a contrary intention is apparent.

As used herein, the terms "comprises," "comprising," "containing" and "having" and the like have the meaning ascribed to them in U.S. Patent law which is open-ended, e.g., "including at least" and the like; "consisting essentially of" or "consists of" likewise has the meaning ascribed in U.S. Patent law, see e.g., AIA Engineering v. Magotteaux, 657 F.3d 1264 (Fed Cir 2011), signifying restriction to excluding prior art elements, e.g., "including only," however allowing for the presence of more than that which is recited so long as the additional elements do not materially affect the basic and novel properties of the invention. For example, the term, "consisting essentially of" in relation to a nucleic acid sequence refers to the nucleic acid of that sequence length or equivalents thereof.

Prior to describing the various embodiments, the following definitions are provided and should be used unless otherwise indicated.

"Subject" means any animal, but is preferably a mammal, such as, for example, a human, monkey, mouse, or rabbit.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

Ascorbic acid refers to the compound (R)-5-((S)-1,2-dihydroxyethyl)-3,4-dihydroxyfuran-2(5H)-one or salts thereof. It is also contemplated that derivatives such as esters of the hydroxy groups could be used for the applications disclosed herein. For example any of the hydroxy groups of ascorbic acid could contain a fatty acid group. In certain embodiments, other esters, phosphates or other groups labile to acid hydrolysis or cellular esterases could be utilized, e.g., ascorbyl palmitate, magnesium ascorbyl phosphate, ascorbyl tetra-isopalmitoyl, tetrahexyldecyl ascorbate, sodium ascorbyl phosphate, trisodium ascorbate-2-phosphate, ascorbyl dipalmitate, ascorbyl stearate. In certain embodiments, derivatives such as erythorbic acid and salts thereof are contemplated.

Bone morphogenetic protein 4 (BMP-4) is a TGF-beta superfamily ligand. The human BMP-4 precursor contains a 273 amino acid (aa) propeptide and a 116 aa mature protein, e.g., a human mature BMP-4 sequence is SPKHHPQR SRKKNKNCRR HSLYVDFSDV GWNDWIVAPP GYQA-FYCHGD CPFPLADHLN STNHAIVQTLVNSVNSSIPK ACCVPTELSA ISMLYLDEYD KVVLKNYQEM VVEG-CGCR (SEQ ID NO: 138). Processing of the propeptide by furin or proprotein convertase 6 enables the formation of the mature disulfide-linked homodimeric BMP-4 and facilitates its secretion. Experiments herein utilized BMP-4 as the secreted disulfide-linked homodimeric BMP-4.

Mature human and mouse BMP-4 share 98% amino acid sequence identity. Human BMP-4 shares 85% amino acid sequence identity with human BMP-2 and less than 50% with other human BMPs. The human protein and homologs typically have greater than 90 or 95% sequence identity to the human sequence. Bone morphogenetic proteins were originally identified by an ability of demineralized bone extract to induce endochondral osteogenesis. It is contemplated that fragments and variants could also retain activity which can be identified by routine testing using protocols reported herein. For example, in certain embodiments, the disclosure contemplates that active fragments are greater than or smaller than 50, 60, 70, 80, 90, 100, or 110 continuous amino acids of SEQ ID NO: 138 or variants. Variants may be a similar protein comprising one, two, three, four, five, six, seven, eight, nine, ten, eleven, twelve, thirteen, fourteen, fifteen, sixteen, seventeen, eighteen, nineteen, twenty, twenty one, twenty two, twenty three, twenty four, twenty five, twenty six, twenty seven, twenty eight, twenty nine, thirty or more amino acids substitutions, deletions, insertions, or combinations thereof, in certain embodiments, the substitutions are conserved substitutions. In certain embodiments, the substitutions or conserved substitutions are or are not in a functional domain.

As used herein, the term "nucleic acid" is intended to mean a ribonucleic or deoxyribonucleic acid or analog thereof. A nucleic acid can include native or non-native bases. In this regard a native deoxyribonucleic acid can have one or more bases selected from the group consisting of adenine, thymine, cytosine or guanine and a ribonucleic acid can have one or more bases selected from the group consisting of uracil, adenine, cytosine or guanine. It will be understood that a deoxyribonucleic acid used in the methods or compositions set forth herein can include uracil bases and a ribonucleic acid can include a thymine base. Exemplary non-native bases that can be included in a nucleic acid, whether having a native backbone or analog structure, include, without limitation, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. A particular embodiment can utilize isocytosine and isoguanine in a nucleic acid in order to reduce non-specific hybridization, as generally described in U.S. Pat. No. 5,681, 702.

A non-native base used in a nucleic acid can have universal base pairing activity, wherein it is capable of base pairing with any other naturally occurring base. Exemplary bases having universal base pairing activity include 3-nitropyrrole and 5-nitroindole. Other bases that can be used include those that have base pairing activity with a subset of the naturally occurring bases such as inosine, which base-pairs with cytosine, adenine or uracil. Alternatively or additionally, oligonucleotides, nucleotides or nucleosides including the above-described non-native bases can further include reversible blocking groups on the 2', 3' or 4' hydroxyl of the sugar moiety.

It is believed that microRNAs are initially transcribed as part of one arm of an about 80 nucleotide RNA stem-loop (termed a primary microRNA or pri-miRNA). Each pri-miRNA may contain several microRNA precursors that potentially undergo processing and cleavage by proteins and enzymes to form precursor microRNAs (pre-miRNAs). Pre-miRNAs are then exported out of the nucleus and into the cytoplasm where the pre-miRNA hairpin is cleaved by an RNase enzyme (Dicer). Dicer is thought to interact with the 3' end of the hairpin and cuts away the loop joining the 3' and 5' arms resulting in an unstable microRNA duplex, and ultimately resulting in a mature miR-3p and miR-5p. The microRNA database (http://www.mirbase.org/) reports Mus musculus (mmu):

```
miR-208b-3p as
                                  (SEQ ID NO: 1)
AUAAGACGAACAAAAGGUUUGU, mmu-miR-499-5p as
                                  (SEQ ID NO: 3)
UUAAGACUUGCAGUGAUGUUU
and mmu-miR-1a-2-5p as
                                  (SEQ ID NO: 134)
ACAUACUUCUUUAUGUACCCAUA.
```

Sequences disclosed herein may be used in the processes disclosed herein as whole 20 to 22 base oligonucleotides or fragments, 5, 8, 10, 15 to 20 nucleobase long fragments that are less than the entire sequence, or by adding nucleotides on the ends or as the primary microRNA with the expectation of cellular processing to the mature forms. Also contemplated are that these sequences are encoded within a nucleic acid configure for expression in the cells by being in operable combination with a promotor region.

The term "nucleobase polymer" refers to a polymer comprising nitrogen containing aromatic or heterocyclic bases that are capable of binding to naturally occurring nucleic acids through hydrogen bonding otherwise known as base pairing. A typical nucleobase polymer is a nucleic acid, RNA, DNA, or chemically modified form thereof. A nucleic acid may be single or double stranded or both, e.g., they may contain overhangs. Nucleobase polymers may contain naturally occurring or synthetically modified bases and backbones. In certain embodiments, a nucleobase polymer need not be entirely complementary, e.g., may contain one or more insertions, deletions, or be in a hairpin structure provided that there is sufficient selective binding.

With regard to the nucleobases, it is contemplated that the term encompasses isobases, otherwise known as modified bases, e.g., are isoelectronic or have other substitutes configured to mimic naturally occurring hydrogen bonding base-pairs. For Example, U and T are isobases. Within any of the sequences disclosed herein U may be substituted for T, or T may be substituted for U. Examples of nucleotides with modified adenosine or guanosine include, but are not limited to, hypoxanthine, xanthine, 7-methylguanine. Examples of nucleotides with modified cytidine, thymidine, or uridine include 5,6-dihydrouracil, 5-methylcytosine, 5-hydroxymethylcytosine. Contemplated isobases include 2'-deoxy-5-methylisocytidine (iC) and 2'-deoxy-isoguanosine (iG) (see U.S. Pat. No. 6,001,983; U.S. Pat. No. 6,037,120; U.S. Pat. No. 6,617,106; and U.S. Pat. No. 6,977,161). In another embodiment, a removable base (such as uracil or 8-oxoguanine) is contemplated so that treatment by uracil-DNA glycosylase (UDG) or formamidopyrimidine-DNA glycosylase (FPG), can lead to cleavage and degradation of unwanted sequences.

In order to prevent in vivo breakdown, nucleobase polymers or nucleic acids may be chemically modified, e.g., within the sugar backbone or on the 5' or 3' ends. As such, in certain embodiments, nucleobase polymers disclosed herein may contain monomers of phosphodiester, phosphorothioate, methylphosphonate, phosphorodiamidate, piperazine phosphorodiamidate, ribose, 2'-O-methy ribose, 2'-O-methoxyethyl ribose, 2'-fluororibose, deoxyribose, 1-(hydroxymethyl)-2,5-dioxabicyclo[2.2.1]heptan-7-ol, P-(2-(hydroxymethyl)morpholino)-N,N-dimethylphosphonamidate, morpholin-2-ylmethanol, (2-(hydroxymethyl) morpholino) (piperazin-1-yl)phosphinate, or peptide nucleic acids or combinations thereof.

Within any of the sequences disclosed herein, U may be T or T may be U. In certain embodiments, a variant fragment is greater than 5, 10, 15, or 20 nucleotides or nucleobases but less than 100, 50, or 25.

In certain embodiments, the nucleobase polymer is single or double stranded RNA that is 3' end capped with one, two, or more thymidine nucleotides and/or the passenger strand of the RNA comprises 5' end polyphosphate, e.g., di-phosphate, tri-phosphate.

In certain embodiments, the nucleobase polymer is non-naturally occurring because it contains at least one sugar modification, phosphate modification, nucleotide base modification.

In certain embodiments, the nucleobase polymer is non-naturally occurring because it contains at least one nucleotide with the following formula:

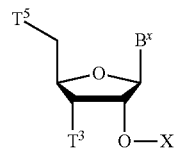

wherein:

Bfx is adenine, guanine, hypoxanthine, uracil, thymine, cytosine, 2-aminoadenine or 5-methylcytosine;

$T^3$ and $T^5$, independently, are OH, a nucleotide, a nucleoside, or an oligonucleotide;

X is $R^1$-$R^2$;

$R^1$ is $C_1$-$C_{20}$ alkyl; and $R^2$ is O-alkyl, S-alkyl, NH-alkyl, or N-dialkyl.

In certain embodiments, X is 2-methoxyethyl.

Sequence "identity" refers to the number of matching nucleotides (expressed as a percentage) in a sequence alignment between two sequences of the alignment window. As used herein, percentage identity of an alignment is calculated using the number of identical positions divided by the greater of the shortest sequence or the number of equivalent positions excluding overhangs (no nucleotide or not matching) wherein internal gaps are counted as an equivalent position. For example the nucleotide CCCCCC (SEQ ID NO: 67) and CCACC (SEQ ID NO: 68) have a sequence identity of 4 out of 5 or 80%. For example, the polypeptides CCCTTT (SEQ ID NO: 69) and CCCATTT (SEQ ID NO: 110) have a sequence identity of 6 out of 7 or 85%. In another example, comparison of AUAAGACGAACAA-AAGGUUUGU (SEQ ID NO: 1) (dash is an internal gap) and UUAAGACUUGCAGUGAUGUUU (SEQ ID NO: 3) provides underlined identical positions 13 out of 20 or 65% identity.

As used herein, the term "cell" refers to a eukaryotic cell, i.e., having a nucleus comprising chromosomes, mitochondria, and other organelles. Certain embodiments of the disclosure exemplify fibroblasts or fibrocytes which are cells that typically synthesis collagen and express the protein vimentin. In certain embodiment, the disclosure contemplates the utilization of human fibroblasts derived from skin, blood, urine derived mesenchymal stem cells, embryonic stem cells (ESCs), induced pluripotent stem cells (iPS), multipotent mesenchymal stem cells (MSCs), bone marrow, bone marrow-derived mesenchymal stromal cells (BMSC), adipose-derived stem cells (ASCs), hair follicle stem cells, and amniotic fluid stem cells.

Methods for isolating human dermal fibroblast are outlined in Zhao et al., Preliminary survival studies on autologous cultured skin fibroblasts transplantation by injection, Cell Transplant, 2008, 17(7):775-83; Lui et al., A novel bioreactor microcarrier cell culture system, Cell Transplant, 2006, 15:435-443; and Lui et al., High yields of autologous living dermal equivalents using porcine gelatin microbeads. Cell Transplant, 2006, 15:445-451. In a typical procedure, skin biopsies are cut into pieces and digested with dispase. One separates the dermis from the epidermis. The dermis is incubated in Dulbecco's modified Eagles medium supplemented with oxygen and heat-inactivated fetal bovine serum. Penicillin, streptomycin, and glutamine, are also added. Fibroblasts grow out of skin segments in the culture over a week. Fibroblast cells are treated with trypsin to detach fibroblasts and collected by centrifugation which can be further replicated/subcultured under similar conditions.

Urine derived cells may be prepared by processes provided in Bharadwaj et al., Multipotential differentiation of human urine-derived stem cells: Potential for therapeutic applications in urology, Stem Cells, 2013, 31: 1840-1856. Urine samples are centrifuged and cell pellets are washed with phosphate buffered saline. The cells are cultured in keratinocyte serum-free medium (KSFM) and embryonic fibroblast medium (EFM) mixed at a ratio of 1:1 with 5% fetal bovine serum (FBS). Plates that contained single cells were cultured for additional propagation. During propagation cells may be selected for mesenchymal stem cell markers (CD29, CD44, CD54, CD73, CD90, CD105, CD166 and STRO-1).

In certain embodiments, other contemplated cells for use in methods disclosed herein such as blood or bone marrow cells, cardiac or cardiac precursor cells, epithelial cells, stem cells, induced pluripotent cells, endothelial cells, endothelial precursor cells, embryonic stem (ES) cells, embryoid body cells, cells isolated from bone marrow or peripheral blood by selecting cells that express CD31 and/or CD34, preferably a mammalian or human cell, Inserting a nucleobase polymer or nucleic acid with the same sequence may be done by any method known in the art. For example a nucleobase polymer or oligonucleotide comprising or consisting essentially of the miRNA of SEQ ID NO: 1-134 or variants thereof may be prepared for insertion into the cell by lipofection, i.e., mixing with a cationic lipid such as O-(2R-1,2-di-O-(1'Z, 9'Z-octadecadienyl)-glycerol)-3-N-(bis-2-aminoethyl)-carbamate, Bis-guanidinium-spermidine-cholesterol, Bis-guanidinium-tren-cholesterol, N-1-cholesteryloxycarbonyl-3,7-diazanonane-1,9-diamine, Cholesteryl hemidithiodiglycolyl tris(aminoethyl)amine, O-(1,2-di-O-(9'Z-octadecenyl)-glycerol)-3-N-(bis-2-aminoethyl)-carbamate, 3β-[N—(N', N'-Dimethylaminoethyl)carbamoyl]cholesterol, O,O'-Dilauryl N-lysylaspartate, O,O'-Dimyristyl N-lysylaspartate, Dioleylglycerol, Dioctadecylamidoglycylspermine (Transfectam®), 1,2-Dioleoyl-sn-glycero-3-succinyl-2-hydroxyethyl disulfide ornithine, 1,2-Dioleoyl-sn-glycero-3-phosphocholine, 1,2-Dioleoyl-sn-glycerol-3-phosphoethanolamine, Dioleyl succinyl ethylthioneomycin, Dioleyl succinyl paromomycin, Dioleyl succinyl tobramycin, 1,2-Dioleoyl-3-trimethylammoniopropane, N'-[1-(2,3-Dioleyloxy)propyl]-N,N,N-trimethylammonium chloride, Di-palmitoyl phosphatidylethanolamidospermine, Di(octadec-9-ynoyl)phosphatidyl ethanolamine, 1,2-Dioleoyl-sn-3-ethylphosphocholine, or those as reported in Labas et al., Nature as a source of inspiration for cationic lipid synthesis, Genetica, 2010, 138(2):153-68.

A procedure for the preparation of lipid and oligonucleotide complex typically entails suspending the cationic lipid in aqueous buffer and sonication to form small vesicles. The cationic lipid vesicles are mixed with the aqueous oligonucleotide solution at a weight ratio of 10:1, lipid:oligonucleotide, and incubated for a period of time. During this incubation it is presumed that the positively charged liposomes associate and coat the surface of the oligonucleotide, giving the oligonucleotide a cationic lipid layer which facilitates interaction with and transfer through the cell membrane. With small oligonucleotide fragments or oligomers, the oligonucleotide is typically smaller than the lipid particle. In this case, the lipid does not coat the oligonucleotide, but rather the oligonucleotide coats the surface of the liposome. This would serve to disrupt the liposome: cell surface interaction and inhibit transfer through the membrane. To effectively coat these oligonucleotide particles, the lipid is presented to the oligonucleotide in its monomer (or small aggregate) form. This can be accomplished by dissolving the lipid in an organic solvent and either dispersing the organic in an aqueous solution of the oligonucleotide, or incubating the lipid and oligonucleotide together in the organic solvent. The solvent of choice is ethanol since it is both miscible with water and non-toxic to biological systems in the event that residual solvent remains in the suspension.

The oligonucleotide and the cationic lipids may be mixed separate from the cell to form a complex or micelle or particle and then mixed with the cell. Optionally the oligonucleotide, cationic lipids, and cells may be mixed together.

In certain embodiments, it is contemplated that the nucleobase polymer or nucleic acid may be inserted into the cell for expression using an appropriate vector. A recombinant virus, plasmid, or other vector may be designed such that it can enter the cell and express the nucleobase polymer. The nucleobase polymer or nucleic acid may be surrounded by a particle made up of viral proteins, i.e., virus particle or virus-like particle, or cationic lipids that are attached to molecules that interact with the cell facilitating entry.

As used herein, nucleobase polymer or nucleic acid "variants" refer to a change in the nucleotide base sequence. For example, in certain embodiments, variants of a sequence may have greater than 50%, 60%, 65%, 70%, 75%, 80%, 85%, 90%, 95%, 97%, 97%, 98%, or 99% sequence identity considering isobases as equivalent nucleotides. Contemplated variants of AUAAGACGAACAAAAGGUUUGU (SEQ ID NO: 1), are provided below wherein any U may be individually at each position, U or T.

UUAAGACUUGCAGUGAUGUUU, (SEQ ID NO: 3)

AUAAGACGAACAAAAGGUUUG, (SEQ ID NO: 4)

AUAAGACGAACAAAAGGUU, (SEQ ID NO: 5)

AUAAGACGAACAAAAGGU, (SEQ ID NO: 6)

AUAAGACGAACAAAAGG, (SEQ ID NO: 7)

UAAGACGAACAAAAGGUUUGU, (SEQ ID NO: 8)

AAGACGAACAAAAGGUUUGU, (SEQ ID NO: 9)

AGACGAACAAAAGGUUUGU, (SEQ ID NO: 10)

GACGAACAAAAGGUUUGU, (SEQ ID NO: 11)

ACGAACAAAAGGUUUGU, (SEQ ID NO: 12)

UAAGACGAACAAAAGGUUUG, (SEQ ID NO: 13)

UAAGACGAACAAAAGGUUU, (SEQ ID NO: 14)

UAAGACGAACAAAAGGUU, (SEQ ID NO: 15)

UAAGACGAACAAAAGGU, (SEQ ID NO: 16)

AAGACGAACAAAAGGUUU, (SEQ ID NO: 17)

AAGACGAACAAAAGGUU, (SEQ ID NO: 18)

AGACGAACAAAAGGUUUG, (SEQ ID NO: 19)

AGACGAACAAAAGGUUU, (SEQ ID NO: 20)

GACGAACAAAAGGUUUG, (SEQ ID NO: 21)

AUAAGACUAACAAAAGGUUUG, (SEQ ID NO: 22)

AUAAGACUAACAAAAGGUUU, (SEQ ID NO: 23)

AUAAGACUAACAAAAGGUU, (SEQ ID NO: 24)

AUAAGACUAACAAAAGGU, (SEQ ID NO: 25)

AUAAGACUAACAAAAGG, (SEQ ID NO: 26)

UAAGACUAACAAAAGGUUUGU, (SEQ ID NO: 27)

AAGACUAACAAAAGGUUUGU, (SEQ ID NO: 28)

AGACUAACAAAAGGUUUGU, (SEQ ID NO: 29)

GACUAACAAAAGGUUUGU, (SEQ ID NO: 30)

ACUAACAAAAGGUUUGU, (SEQ ID NO: 31)

UAAGACUAACAAAAGGUUUG, (SEQ ID NO: 32)

UAAGACUAACAAAAGGUUU, (SEQ ID NO: 33)

UAAGACUAACAAAAGGUU, (SEQ ID NO: 34)

UAAGACUAACAAAAGGU, (SEQ ID NO: 35)

AAGACUAACAAAAGGUUU, (SEQ ID NO: 36)

AAGACUAACAAAAGGUU, (SEQ ID NO: 37)

AGACUAACAAAAGGUUUG, (SEQ ID NO: 38)

AGACUAACAAAAGGUUU, (SEQ ID NO: 39)

GACUAACAAAAGGUUUG, (SEQ ID NO: 40)

AUAAGACUUACAAAAGGUUUG, (SEQ ID NO: 41)

AUAAGACUUACAAAAGGUUU, (SEQ ID NO: 42)

AUAAGACUUACAAAAGGUU, (SEQ ID NO: 43)

AUAAGACUUACAAAAGGU, (SEQ ID NO: 44)

AUAAGACUUACAAAAGG, (SEQ ID NO: 45)

UAAGACUUACAAAAGGUUUGU, (SEQ ID NO: 46)

AAGACUUACAAAAGGUUUGU, (SEQ ID NO: 47)

AGACUUACAAAAGGUUUGU, (SEQ ID NO: 48)

GACUUACAAAAGGUUUGU, (SEQ ID NO: 49)

ACUUACAAAAGGUUUGU, (SEQ ID NO: 50)

UAAGACUUACAAAAGGUUUG,          (SEQ ID NO: 51)

UAAGACUUACAAAAGGUUU,           (SEQ ID NO: 52)

UAAGACUUACAAAAGGUU,            (SEQ ID NO: 53)

UAAGACUUACAAAAGGU,             (SEQ ID NO: 54)

AAGACUUACAAAAGGUUU,            (SEQ ID NO: 55)

AAGACUUACAAAAGGUU,             (SEQ ID NO: 56)

AGACUUACAAAAGGUUUG,            (SEQ ID NO: 57)

AGACUUACAAAAGGUUU,             (SEQ ID NO: 58)

GACUUACAAAAGGUUUG,             (SEQ ID NO: 59)

AUAAGACGAGCAAAAGGUUUG,         (SEQ ID NO: 60)

AUAAGACGAGCAAAAGGUUU,          (SEQ ID NO: 61)

AUAAGACGAGCAAAAGGUU,           (SEQ ID NO: 62)

AUAAGACGAGCAAAAGGU,            (SEQ ID NO: 63)

AUAAGACGAGCAAAAGG,             (SEQ ID NO: 64)

UAAGACGAGCAAAAGGUUUGU,         (SEQ ID NO: 65)

AAGACGAGCAAAAGGUUUGU,          (SEQ ID NO: 66)

AGACGAGCAAAAGGUUUGU,           (SEQ ID NO: 70)

GACGAGCAAAAGGUUUGU,            (SEQ ID NO: 71)

ACGAGCAAAAGGUUUGU,             (SEQ ID NO: 72)

UAAGACGAGCAAAAGGUUUG,          (SEQ ID NO: 73)

UAAGACGAGCAAAAGGUUU,           (SEQ ID NO: 74)

UAAGACGAGCAAAAGGUU,            (SEQ ID NO: 75)

UAAGACGAGCAAAAGGU,             (SEQ ID NO: 76)

AAGACGAGCAAAAGGUUU,            (SEQ ID NO: 77)

AAGACGAGCAAAAGGUU,             (SEQ ID NO: 78)

AGACGAGCAAAAGGUUUG,            (SEQ ID NO: 79)

AGACGAGCAAAAGGUUU,             (SEQ ID NO: 80)

GACGAGCAAAAGGUUUG,             (SEQ ID NO: 81)

AUAAGACGAACAGAAGGUUUG,         (SEQ ID NO: 82)

AUAAGACGAACAGAAGGUUU,          (SEQ ID NO: 83)

AUAAGACGAACAGAAGGUU,           (SEQ ID NO: 84)

AUAAGACGAACAGAAGGU,            (SEQ ID NO: 85)

AUAAGACGAACAGAAGG,             (SEQ ID NO: 86)

UAAGACGAACAGAAGGUUUGU,         (SEQ ID NO: 87)

AAGACGAACAGAAGGUUUGU,          (SEQ ID NO: 88)

AGACGAACAGAAGGUUUGU,           (SEQ ID NO: 89)

GACGAACAGAAGGUUUGU,            (SEQ ID NO: 90)

ACGAACAGAAGGUUUGU,             (SEQ ID NO: 91)

UAAGACGAACAGAAGGUUUG,          (SEQ ID NO: 92)

UAAGACGAACAGAAGGUUU,           (SEQ ID NO: 93)

UAAGACGAACAGAAGGUU,            (SEQ ID NO: 94)

UAAGACGAACAGAAGGU,             (SEQ ID NO: 95)

AAGACGAACAGAAGGUUU,            (SEQ ID NO: 96)

AAGACGAACAGAAGGUU,             (SEQ ID NO: 97)

AGACGAACAGAAGGUUUG,            (SEQ ID NO: 98)

AGACGAACAGAAGGUUU,             (SEQ ID NO: 99)

GACGAACAGAAGGUUUG,             (SEQ ID NO: 100)

AUAAGACGAACAGUAGGUUUG,         (SEQ ID NO: 101)

AUAAGACGAACAGUAGGUUU,          (SEQ ID NO: 102)

AUAAGACGAACAGUAGGUU,           (SEQ ID NO: 103)

AUAAGACGAACAGUAGGU,            (SEQ ID NO: 104)

AUAAGACGAACAGUAGG,             (SEQ ID NO: 105)

UAAGACGAACAGUAGGUUUGU,         (SEQ ID NO: 106)

AAGACGAACAGUAGGUUUGU,          (SEQ ID NO: 107)

-continued

AGACGAACAGUAGGUUUGU, (SEQ ID NO: 108)

GACGAACAGUAGGUUUGU, (SEQ ID NO: 109)

ACGAACAGUAGGUUUGU, (SEQ ID NO: 111)

UAAGACGAACAGUAGGUUUG, (SEQ ID NO: 112)

UAAGACGAACAGUAGGUUU, (SEQ ID NO: 113)

UAAGACGAACAGUAGGUU, (SEQ ID NO: 114)

UAAGACGAACAGUAGGU, (SEQ ID NO: 115)

AAGACGAACAGUAGGUUU, (SEQ ID NO: 116)

AAGACGAACAGUAGGUU, (SEQ ID NO: 117)

AGACGAACAGUAGGUUUG, (SEQ ID NO: 118)

AGACGAACAGUAGGUUU, (SEQ ID NO: 119)

GACGAACAGUAGGUUUG, (SEQ ID NO: 120)

UUAAGACGAACAAAAGGUUUG, (SEQ ID NO: 121)

UUAAGACGAACAAAAGGUUU, (SEQ ID NO: 122)

UUAAGACGAACAAAAGGUU, (SEQ ID NO: 123)

UUAAGACGAACAAAAGGU, (SEQ ID NO: 124)

UUAAGACGAACAAAAGG, (SEQ ID NO: 125)

UAAGACGAACAAAAGG, (SEQ ID NO: 126)

AAGACGAACAAAAGG, (SEQ ID NO: 127)

AAGACGAACAAAA, (SEQ ID NO: 128)

UAAGACGAACAA, (SEQ ID NO: 129)

UAAGACGAACA, (SEQ ID NO: 130)

UAAGACUAACA, (SEQ ID NO: 131)

UAAGACGUACA, and/or (SEQ ID NO: 132)

UAAGACGAGCA. (SEQ ID NO: 133)

Direct Reprogramming of Fibroblasts into a Cardio-Mimetic Tissue

Heart disease is the leading cause of mortality worldwide. After injury, human postnatal hearts do not recover appropriately, as CMs have limited proliferation capacity. As a new direction of cardiac regenerative therapy, direct reprograming of somatic cells into CM-like cells were developed by introducing a combination of cardiac transcription factors (TFs) or muscle-specific microRNAs (miRNAs). These cells are referred to as induced CMs (iCMs) or cardiac-like myocytes (iCLMs). However, problems still remain for optimal cardiac repair. One study reported inefficiency of generating iCMs in vitro and poor survival of the transplanted iCMs in an infarcted mouse heart. Some studies showed that the direct viral delivery of TFs or miRNAs into heart is effective for cardiac repair, but others reported low efficiency for cardiomyogenesis induced by transplantation of iCM in vivo (1-15%). Another issue is the use of retro- or lenti-viruses for reprogramming, which hinders clinical application. Intriguingly, the role of vascular cells in cardiac repair was not addressed in these studies despite its growing importance in cell survival and cardiac repair. While separate studies reported direct reprogramming of fibroblasts into ECs by lineage-specific TFs1, the roles of miRNAs are unknown. Moreover, no studies reported direct conversion of somatic cells toward multiple cardiovascular cell types.

To address these issues, whether miRNAs can simultaneously reprogram fibroblasts into CMs and vascular cells, i.e. ECs and SMC/PCs, within a tissue-like environment, was investigated. Four types of muscle-specific miRNAs: miR-1, miR-208a, miR-208b, and miR-499, were used. MicroRNAs have advantages over TFs. First, as reprogramming requires changes in expression of numerous genes, and miRNAs may regulate a large group of mRNAs simultaneously, miRNAs may be more efficient reprogramming inducers. Second, there may be potential multicellular reprogramming effects for the above miRNAs, as they are involved in cardiac, not only CM, development. Finally, the availability of miRNA mimics avoids viral use.

Each or all of miR-1a-2-5p, miR-208a-3p, miR-208b-3p, miR-208b-5p, or miR-499-5p mimics were able to induce cardiomyogenic gene expression in mouse dermal fibroblasts. However, miRNA alone was insufficient to generate reprogrammed CMs (rCMs). Addition of ascorbic acid (AA) and BMP4 to miR-1a-2-5p, miR-208b-3p, or miR-499-5p induced sarcomere formation and spontaneous contraction of rCMs. Particularly, miR-208b-3p in these conditions simultaneously induced reprogramming toward EC-like cells (rECs) and SMC/PC-like cells (rSMCs/PCs), and extensive accumulation of ECM. The major component of ECMs was collagen type I. Within ECM, rCMs formed a mass and rECs were invested by rSMCs/rPCs to form durable vascular networks, generating a three-dimensional (3D) cardiac tissue-like structure, CMT. Implantation of this spontaneously constructed CMT onto infarcted mouse heart reduced cardiac strains at early time points and maintained improved cardiac function over 12 weeks. Histologic examination over 16 weeks showed migration of reprogrammed cells from CMT toward the infarcted hearts and robust retention throughout the hearts. Vigorous neovascularization occurred through the concerted actions of both CMT-derived vascular cells (rECs and rSMCs/PCs) and host vascular cells, forming mature vessels over 16 weeks. rCMs initially showed immature characteristics but matured over 16 weeks, particularly at the border zone. This direct tissue reprogramming strategy can be useful for various areas of regenerative medicine by providing essential cardiovascular cells and natural matrix at the same time and bypassing all the complicated processes for individual cell generation and artificial tissue construction.

Experiments herein indicate that one can generate a heart-like tissue consisting of essential cardiovascular cells and ECMs by reprogramming a single terminally differentiated cell type. Conceptually, this study presents the possibility of direct tissue reprogramming from single adult somatic cells, a previously unknown path, and its utility in regenerative medicine. A single muscle-specific miRNA mimic, especially miR 208b, together with AA and BMP generated a cardiac tissue-like patch, CMT, within only 10 days of culture without undergoing a multipotent state. Transplantation of CMT on the infarct hearts significantly improved post-MI cardiac function through enhanced cell retention, neovascularization, and cardiomyogenesis. Long-term follow-up studies showed maturation of CMT-derived cardiomyocytes and vascular structures.

This multi-lineage tissue reprogramming presents an important advance in cardiac cell therapy by meeting the major needs of the current approach. It is well known that transplantation of a single cell type has limited potency due to low cell retention and lack of interaction with other supportive cells. Thus, the following approaches have been attempted and have shown more favorable results: biomaterial-mediated cell delivery, addition of supportive cells such as ECs and/or fibroblasts, and a combination of biomaterial and these supportive cells. The biomaterial provides a protective environment for cell survival and the supportive cells enhance cellular cross-talk, vascularization, and cell survival and function in the infarcted area. CMT provides all these cells and natural matrix at the same time, bypassing all the complicated processes needed for artificial tissue construction.

Five miRNA mimics, miR-1a-2-5p, miR-208a-3p, miR-208b-3p, miR-208b-5p and miR-499-5p, were employed alone or together. Each of these miRNAs reprogrammed fibroblasts toward a CM phenotype. A prior study indicated that a combination of miRNAs-1, -133, -208, and -499 generated more mature iCMs than a single miRNA. See Jayawardena et al. MicroRNA-mediated in vitro and in vivo direct reprogramming of cardiac fibroblasts to cardiomyocytes. Circulation research, 2012, 110, 1465-1473. However, experiments reported herein indicate that a single miR-208b-3p is more efficient than combinations. In the presence of AA and BMP4, three single miRNA mimics, miR-1a-2-5p, miR-208b-3p, and miR-499-5p, induced beating CMs, with miR-208b-3p the most efficient. Surprisingly, all of these miRNAs induced reprogramming toward ECs, and miR-208b-3p toward SMCs, even without AA and BMP4. These results provide the first evidence for a role of miRNAs in reprogramming fibroblasts into ECs or SMCs. Addition of AA and BMP4 to miR-1a-2-5p, miR-208b-3p, or miR-499-5p further developed these rECs into vascular structures.

Experiments herein indicate the importance of AA and BMP4 for tissue generation from reprogrammed cells. Addition of both, but neither alone, induced these effects. Particularly, prolonged treatment with AA and BMP4 stimulated fibroblasts to secrete enough ECMs to form a scaffold and enhance maturation of the reprogrammed cells. AA stimulates biosynthesis of collagen and other ECM components and their cross-linking, enhances CM differentiation of PSCs, and functions as an epigenetic modifier. BMP signaling plays a role in cardiac specification and CM differentiation from human PSCs. Apparently, these two molecules play a key role in the tissue reprogramming process by their pleiotropic effects.

The methods reported herein shown more accelerated and potent reprogramming toward both CMs and vascular cells in vitro compared to other reported method. The rCMs displayed spontaneous contraction from day 4 and sarcomeric striation and calcium oscillations by day 6. In other studies, spontaneous contractions and calcium oscillations appeared after 10 days when using a miRNA cocktail, and after 5 weeks when using cardiac TFs. The rCMs showed characteristics of a mixture of immature and nearly mature CMs. Expression of mature CM genes and proteins, sarcomeric organization, and exhibition of calcium oscillations indicated maturity and functionality, while APs showed an immature pacemaker cell-like phenotype. However, APs may not represent the overall maturity of the rCMs. Due to the difficulties of single cell isolation, APs were measured only in spontaneously contracting cells at day 6, but not after day 6 when ECM deposition and myotube maturation occur. TEM findings such as abundance of mitochondria and formation of clear Z-lines and A- and I-bands further support the maturity of rCMs. Regarding vascular cells, while several groups reported reprogramming of amniotic cells or fibroblasts into ECs using TFs, none of these induced EC-like cells formed tubular structures during in vitro culture. In methods disclosed herein, even when miRNA alone was used, tubular aligned rECs were observed before day 6, and vascular structures were formed after the addition of AA and BMP4 on day 6 and became complex networks by day 10. Experiments herein indicate the formation of functionally mature vessels in various sizes and forms derived from rECs and rSMCs/rPCs in CMT when transplanted in hearts.

The presence of ECMs as well as multiple cell types appears to play a crucial role for expedited reprogramming and enhanced maturation of reprogrammed cells. ECMs provide an environment which enables interactions between cells and exposure to paracrine factors. During heart development, CMs closely interact with fibroblasts, ECs, and SMCs, and these cell-cell interactions in concert with paracrine factors reciprocally stimulate maturation. Experiments herein indicate that the time course of ECM appearance correlated well with rCM maturation and organization of rECs and rSMCs/rPCs.

Transplanted CMT showed clear cardiac regenerative potential. Cell retention, neovascularization, cardiomyogenesis, and paracrine factor secretion all synergistically contributed to enhanced cardiac repair. Paracrine effects and vessel formation were more important in the early phase and cardiomyogenesis in the later phase as underlying the therapeutic effects of CMT. Notably, a large number of cells survived, and this must have played a fundamental role through the entire regenerative process by maximizing the function of the cells and paracrine factors. It is known that bare cell injection results in the death of most injected cells within a week, which severely limits the direct tissue generating and paracrine effects of the cells. The first four weeks after MI is a critical window for determining future cardiac function, as most cardiac cell death happens during this period. At 4 weeks, a large number of transplanted cells still survived, comprising ~11% of the cells in the infarct area, of which 44% were rECs forming various sized vessels. Such a magnitude of surviving transplanted cells rescued endangered myocardial cells by providing paracrine factors for cell survival and by inducing vessel formation to supply oxygen. Numerous hybrid vessels formed by rECs/rSMCs and host vascular cells were observed, suggesting clear interaction between implanted cells and the host vascular system, spanning from capillaries to conduit vessels, which render an effective blood supply throughout the heart. Many vessels were reorganized between 4 to 16 weeks; reactive vessels in the central infarct area disappeared and more CMT-derived vessels were seen at the border and remote zones at 16 weeks. To our knowledge, such strong and mature neovascularization in hearts has not been reported in cell transplantation studies. The contribution of rCMs to cardiac repair is more conspicuous in the border zone. While rCMs made up 42.7% of the total CMT-derived cells at week 4, many of them were localized in the central infarcted area in immature forms and some in the border zone with organized mature forms. At 16 weeks, however, most rCMs were found in the border zone in a fully mature form, indistinguishable from host CMs histologically and forming gap junctions with host CMs. The increased number and maturation of rCMs in the border zones suggest their continuous role in preventing adverse cardiac remodeling and inducing cardiac regeneration over 16 weeks.

These tissue reprogramming procedures and the product, CMT, can serve as a new platform for several key areas in regenerative medicine. First, CMT will be useful for cardiac cell therapy as shown here. CMT has many advantages over current approaches. MicroRNA-induced CMT can avoid the need to separately generate each target cell type, such as CMs or ECs, using complex differentiation or reprogramming processes. Moreover, inherent inclusion of various angiogenic and cell survival factors and preformed vascular networks are additional benefits. CMT can also obviate the need for biomaterials for enhancing cell retention in vivo, a critical issue for any cell therapy. When using biomaterials, many factors including biocompatibility, degradability, inflammation, pore sizes, and cytotoxicity must be considered; however, these are not concerns for CMT as it can be naturally produced from the same host. Moreover, CMT will enable fully autologous cell therapy avoiding immunological reactions, as not only cells but also ECMs can be derived from the same donor. Second, CMT will be useful for disease modeling and investigation. There are many genetic and non-genetic diseases affecting CMs or vessels or both. CMT can offer an effective model to study single or multiple cell types in an environment mimicking cardiac tissues. Third, CMT may serve as a platform to test cardiovascular drugs. CMT has merits over single cells because effects can be tested in multiple cardiovascular cell types simultaneously within a more physiological environment.

Direct Application of Our Reprogramming Agents into the Heart for In Situ Reprogramming In certain embodiments, this disclosure relates to methods of treating a cardiac or vascular disorder comprising administering an effective amount of ascorbic acid or derivative thereof and bone morphogenetic protein 4, optionally in combination with a nucleobase polymer comprising sequence SEQ ID NO: 1 or variants, thereof to a subject in need thereof. In certain embodiments, the nucleobase polymer is administered as a complex with a cationic lipid. In certain embodiments, the nucleobase polymer is encoded in a vector for expression, i.e., a vector comprises a nucleic acid that encodes SEQ ID NO: 1 or variants thereof in operable combination with a promotor. In certain embodiments the combinations of agents are administered directly into a heart muscle, myocardium, epicardium, or endocardium.

In certain embodiments, the methods disclosed herein may be used to treat or prevent in a subject at risk of, exhibiting symptoms of, or diagnosed with any variety vascular diseases such as coronary artery disease, peripheral arterial disease, cerebrovascular disease, renal artery stenosis, aortic aneurysm, cardiomyopathy, hypertensive heart disease, heart failure, pulmonary heart disease, cardiac dysrhythmias, inflammatory heart disease, endocarditis, inflammatory cardiomegaly, myocarditis, valvular heart disease, congenital heart disease, rheumatic heart disease.

EXAMPLES

Reprogramming Adult Mouse Tail-Tip Fibroblasts (MTTFs) Toward CM-Like Cells

The reprogramming potential of muscle-specific miRNA mimics, miR-1a-2-5p, miR-208a-3p, miR-208b-3p, miR-208b-5p, and miR-499-5p was investigated in mouse tail-tip fibroblasts (MTTFs). Each of the miRNA mimics increased expression of CM genes Mef2c, Nkx2-5, Gata4 and Myh6 but not a mesodermal gene Mesp1. Combination of all the miRNAs did not have a synergic effect on gene expression and miR-208b-3p alone was the most effective. Immunocytochemistry confirmed expression of a CM marker sarcomeric α-actinin (ACTN2) in single miRNA transfected cells. However ACTN2 expression was diffuse, sarcomeric organization was poor and spontaneously contracting cells were not observed in any miRNA transfected MTTFs. These results suggested that muscle-specific miRNAs alone are insufficient for reprogramming to CMs.

Figure 1B:
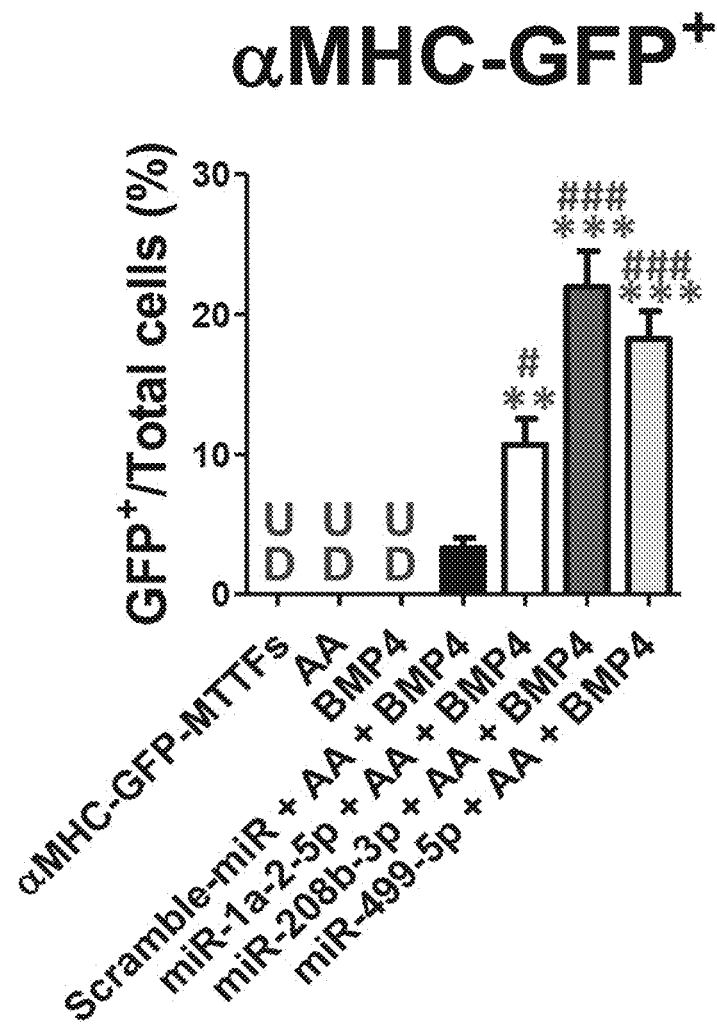
FIG. 1B shows data on the quantitative analyses of aMHC-GFP-positive cells with different combinations of MTTFs, scramble-miR, miR-1a-2-5p, miR-208b-3p, mir-499-59, ascorbic acid, and BMP4.
Figure 1C:
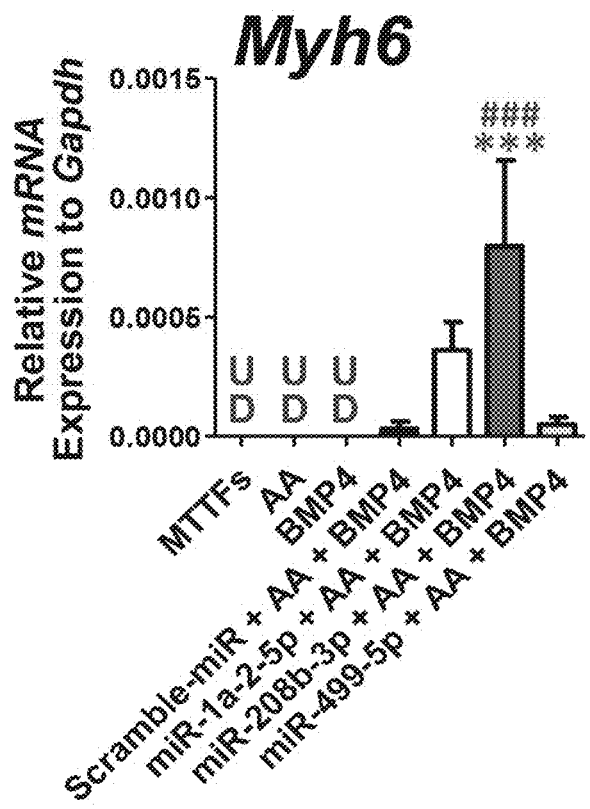
FIG. 1C shows data for mRNA expression of Myh6 (aMHC) with different combinations of MTTFs, scramble-miR, miR-1a-2-5p, miR-208b-3p, mir-499-59, ascorbic acid, and BMP4.
Figure 1D:
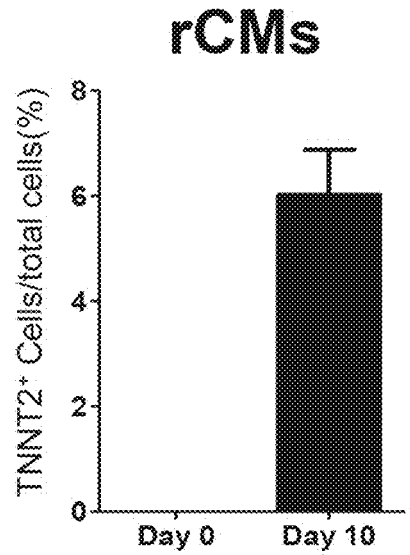
FIG. 1D shows data for quantitative analysis of TNNT2+ cells in MTTFs treated with miR-208b-3p, AA and BMP4 (n=5) at day 10.
Figures 2A, 2B:
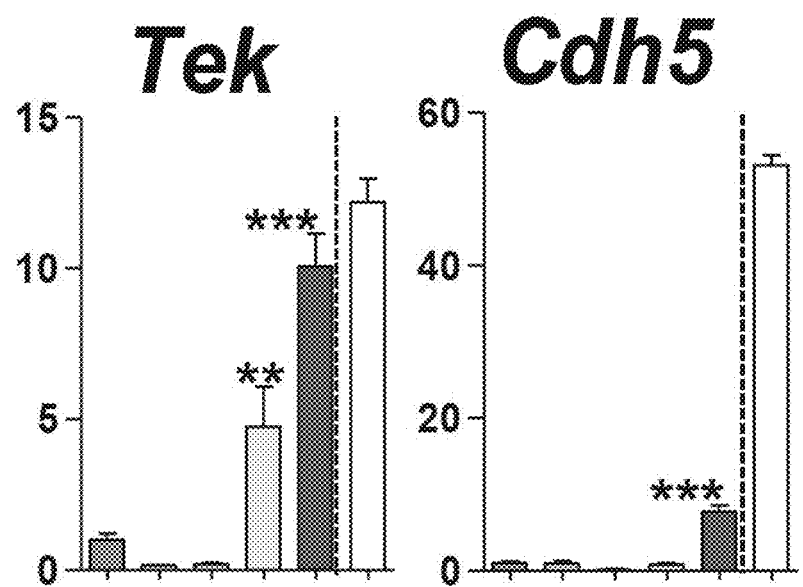
FIG. 2A shows data for relative RNA expression on reprogramming cells into vascular lineage cells using qRT-PCR analyses at day 6 for TEK. Starting from left to right respectively, MTTFs, AA, BMP4, AA and BMP4, AA and BMP4 and miR-208b-3p, heart of adult mouse.
FIG. 2B shows data for relative RNA expression on reprogramming cells into vascular lineage cells using qRT-PCR analyses at day 6 for CDH5. Starting from left to right respectively, MTTFs, AA, BMP4, AA and BMP4, AA and BMP4 and miR-208b-3p, heart of adult mouse.
Figures 2C, 2D:
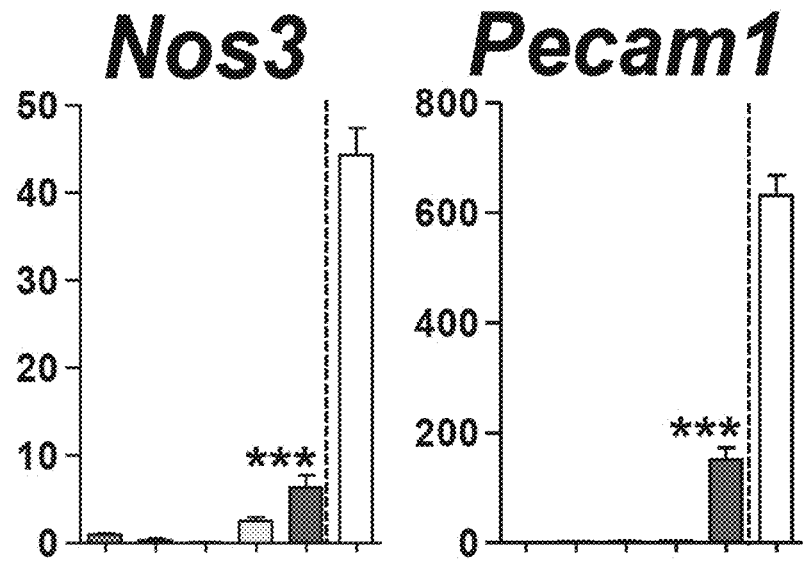
FIG. 2C shows data for relative RNA expression on reprogramming cells into vascular lineage cells using qRT-PCR analyses at day 6 for NOS3. Starting from left to right respectively, MTTFs, AA, BMP4, AA and BMP4, AA and BMP4 and miR-208b-3p, heart of adult mouse.
FIG. 2D shows data for relative RNA expression on reprogramming cells into vascular lineage cells using qRT-PCR analyses at day 6 for PECAM1. Starting from left to right respectively, MTTFs, AA, BMP4, AA and BMP4, AA and BMP4 and miR-208b-3p, heart of adult mouse.
Figure 2E:
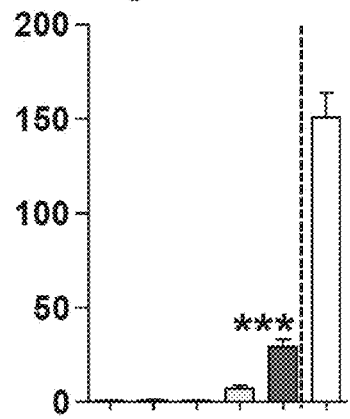
FIG. 2E shows data for relative RNA expression on reprogramming cells into vascular lineage cells using qRT-PCR analyses at day 6 for MYOCD. Starting from left to right respectively, MTTFs, AA, BMP4, AA and BMP4, AA and BMP4 and miR-208b-3p, heart of adult mouse.
Figure 2F:
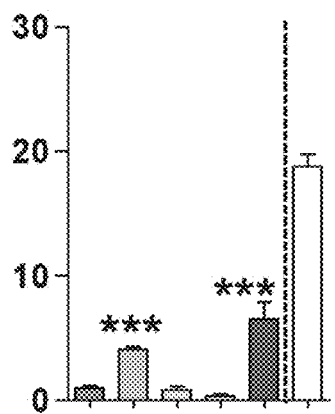
FIG. 2F shows data for relative RNA expression on reprogramming cells into vascular lineage cells using qRT-PCR analyses at day 6 for MYH11. Starting from left to right respectively, MTTFs, AA, BMP4, AA and BMP4, AA and BMP4 and miR-208b-3p, heart of adult mouse.
Figure 4A:
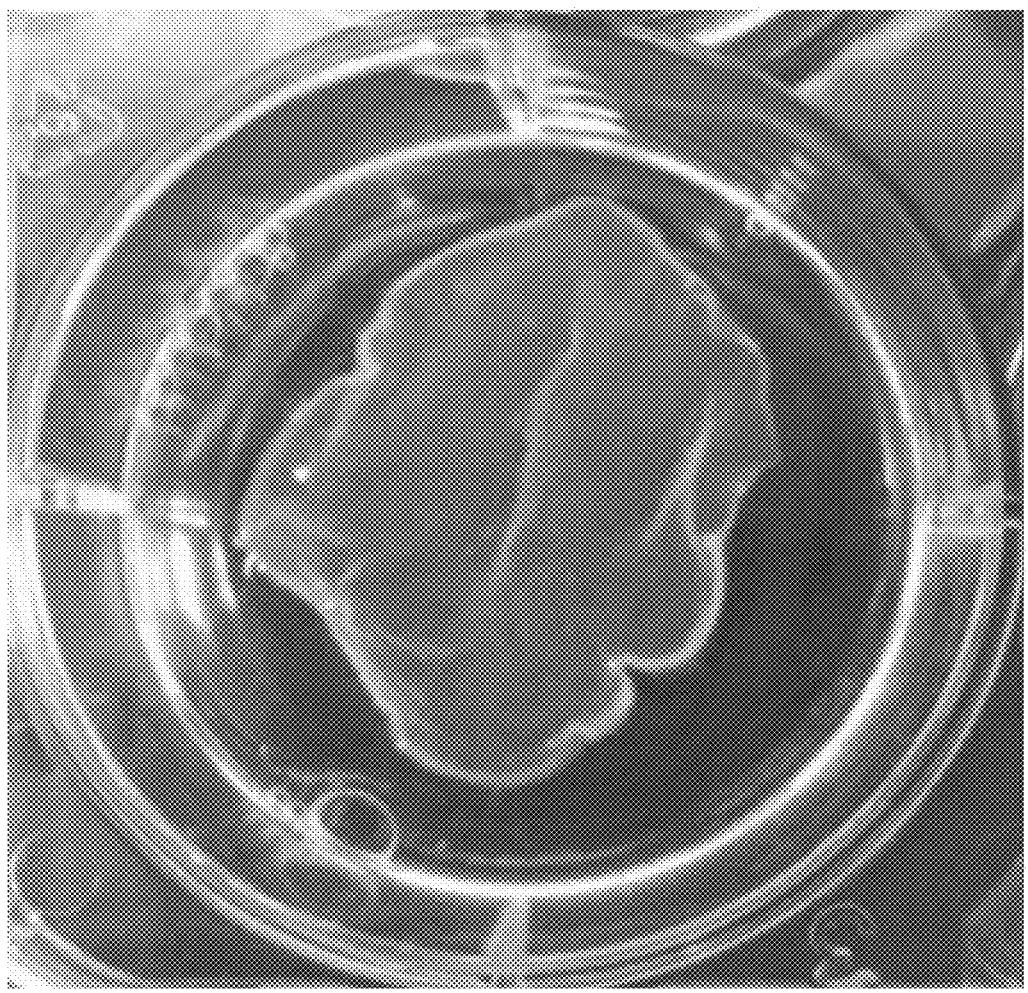
FIG. 4A shows a cardio-mimetic tissue prepared from miR-208b, AA, and BMP-4 at day 10.
Figure 4B:
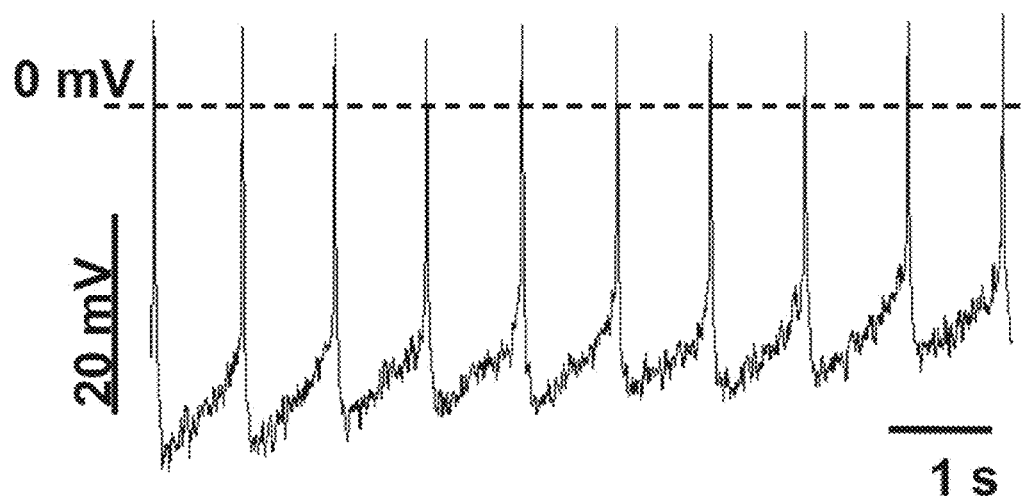
FIG. 4B shows action potentials (APs) measured from spontaneously contracting rCMs at day 6
Figure 5A:
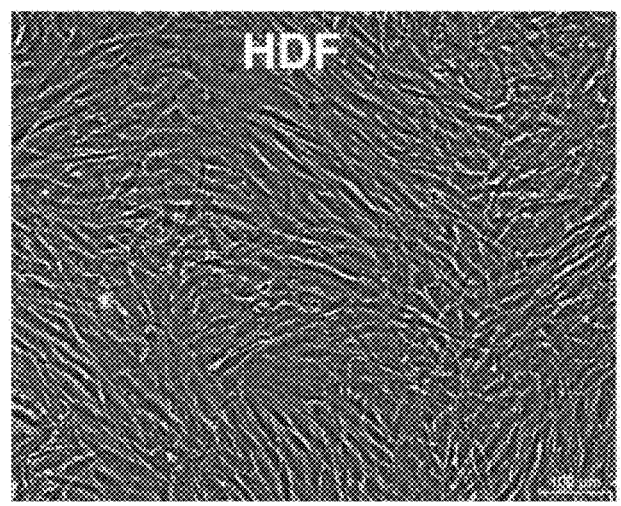
FIG. 5A illustrates the morphological form of Human Dermal Fibroblasts (HDF).
Figure 5B:
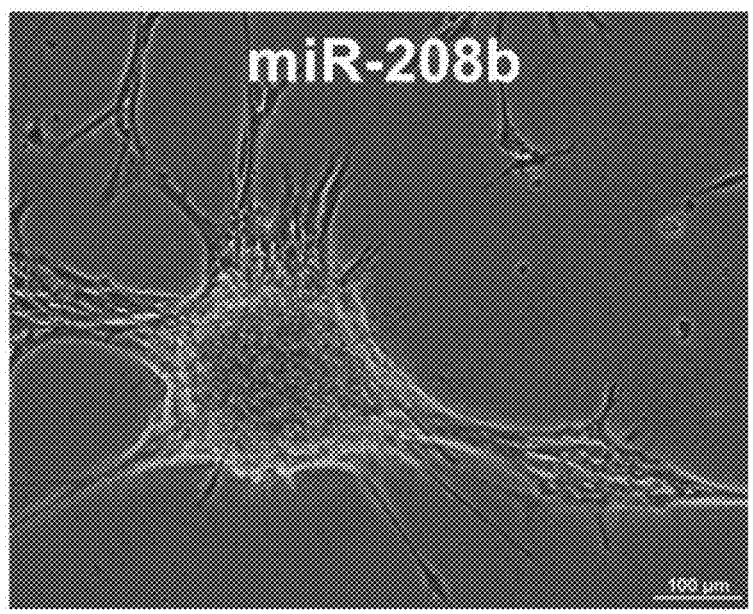
FIG. 5B illustrates the morphological changes of human dermal fibroblasts by miR-208b.

To enhance the reprogramming potential of miRNAs, AA and BMP4 were added one day after miR-transfection (FIG. 1A). Between 4-6 days, spontaneously contracting cells appeared in groups treated with miR-1a-2-3p, miR-208b-3p, or miR-499-5p, but not with miR-208a-3p and miR-208b-5p or all miRNA. The latter groups were excluded from further experiments. To further confirm the results, MTTFs were isolated from aMHC-GFP reporter mice (aMHC-GFP-MT-TFs) and quantified GFP+ cells after treating with miR-1a-2-3p, miR-208b-3p, or miR-499-5p in combination with AA and BMP4. While AA or BMP4 alone did not induce GFP expression and scrambled miRNA plus AA and BMP4 induced GFP expression in <5% of MTTFs, the three selected miRNAs induced GFP expression at a significantly higher rate, with miR-208b-3p yielding the highest (22.0±2.6%) (FIG. 1B) mRNA expression of Myh6 was significantly increased in the miR-208b-3p group with increased trend in the miR-1a-2-5p group (FIG. 1C). However, immunostaining for TNNT showed clear sarcomeric organization in the reprogrammed MTTFs in all miRNA-treated groups. TNNT2+ cells occupied 1.8±0.6% of MTTFs treated with miR-208b-3p, AA and BMP4 by flow cytometry analyses. This reprogramming rate is smaller than the number of aMHC-GFP+ cells because TNNT2 is a more specific and mature marker for CMs. Calcium transient analyses demonstrated spontaneous calcium oscillations in individual cells and the myotube-like structures and synchronous calcium transients between tubular structures, suggesting gap junction formation. A patch clamp study showed immature, early pacemaker cell-like action potentials (APs) (FIG. 4B). Furthermore, transmission electron microscope (TEM) examination showed tightly aligned sarcomeric structures with clear Z-lines, distinguishable A- and I-bands, and abundant mitochondria aligned between sarcomeres, all characteristics of genuine CMs. At day 10, the TNNT2+ cells aggregated to a mass and showed more clear striation, and the number of TNNT2+ cells was increased to about 6% of the total cells (FIG. 1C). Based on these data, these cells are referred to as reprogrammed CMs (rCMs). These experiments indicate that a single miRNA mimic, either miR-1a-2-5p, miR-208b-3p or miR-499-5p, could reprogram MTTFs toward functional CM-like cells within a week when AA and BMP4 were added and miR-208b-3p is the most potent.

Reprogramming into Vascular-Lineage Cells

Whether the protocol with miR-208b-3p induced other lineage conversion was investiged, and mRNA expression was measured for the following markers at day 6: pluripotent stem cell (Pou5f1, Sox2 and Nanog), mesoderm (Mesp1), ectoderm (Nestin), endoderm (Foxa2a), ECs (Vwf, Kdr, Tek, Cdh5, Nos3 and Pecam1) and SMCs (Acta2, Tagln, Cald1, Calm1, Myocd and Myh11). qRT-PCR showed increased expression of EC and SMC genes but no other lineage genes (FIG. 2A-F).

Between day 6 to 10, multi-branched structures appeared and expanded gradually, forming networks, and these structures stained positive for TEK, PECAM1, and CDH5, indicating emergence of rECs. Furthermore, these rECs take up DiI-Ac-LDL in both natural and enzyme-mediated dissociated status. By flow cytometry, ~5% and 37% of cells were positive for DiI-Ac-LDL at day 6 and 10, suggesting an expansion of rECs over time. In addition, a nitric oxide indicator DAF-FM diacetate was detected in the tubular structures. These data suggest functional activity of rECs. Double immunostaining of ACTA2, SM22a or PDGFRB, a SMC/PC marker, with either PECAM1 or CDH5 showed abundant SMC/PC-like cells surrounded the vascular networks consisting of rECs. Taken together, these data indicate that miR-208b-3p plus AA and BMP4 induced reprogramming of fibroblasts into functional EC and SMCs/PCs.

Generation of Cardio-Mimetic Tissue

Between day 6 to 10, spontaneous deposition of extracellular matrices (ECMs), forming three-dimensional (3D) tissue-like patches was unexpectedly found (FIG. 4A)—cardiomimetic tissue (CMT). CMT generated at day 10 was used in the future experiments. Cell aggregation and ECM deposition were confirmed by Masson's trichrome staining. Fluorescence microscopic examination before and after decellularization further confirmed tight integration of cells and ECM in the 3D structure. A PCR array for 84 genes related to ECMs and adhesion molecules demonstrated that 31 genes including 4 collagen isoforms and 9 MMPs were up-regulated and 2 genes were down-regulated in the CMT compared to MTTFs. Liquid chromatography-mass spectrometry (LCMS) showed that ~51% of the matrix consists of collagen isoforms with collagen type I being the most abundant. Collagen type I is the most common ECM protein in the normal heart. These data demonstrate that ECM deposition along with multicellular reprogramming leads to formation of artificial cardiovascular tissue.

Therapeutic Effects of CMT

Figure 3A:
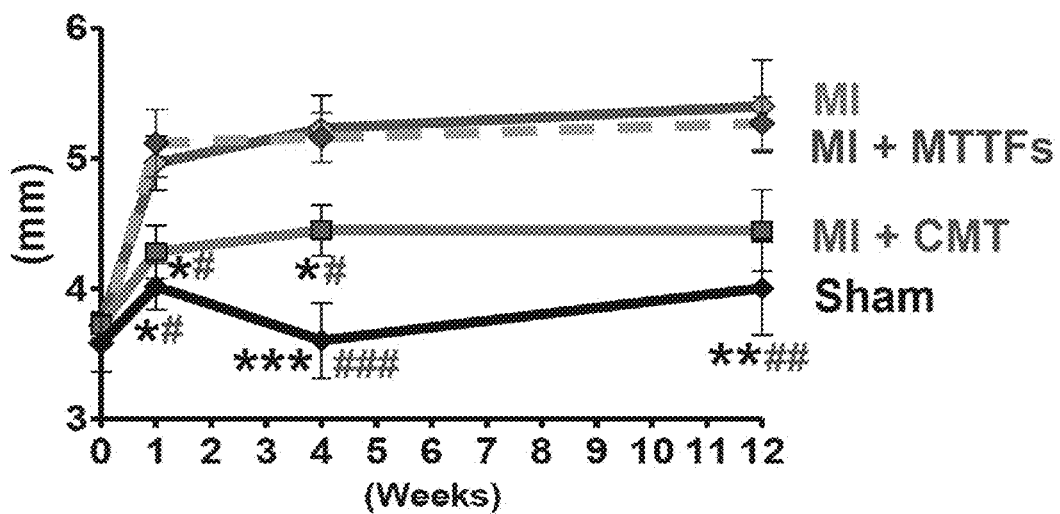
FIG. 3A shows echocardiographic analyses (comparisons of LV end-diastolic dimension (LVEDD)) before and 1, 4 and 12 weeks after the Transplantation of CMT on MI heart with no injection (MI), MTTFs (MI and MTTF5), CMT (MI and CMT).
Figure 3B:
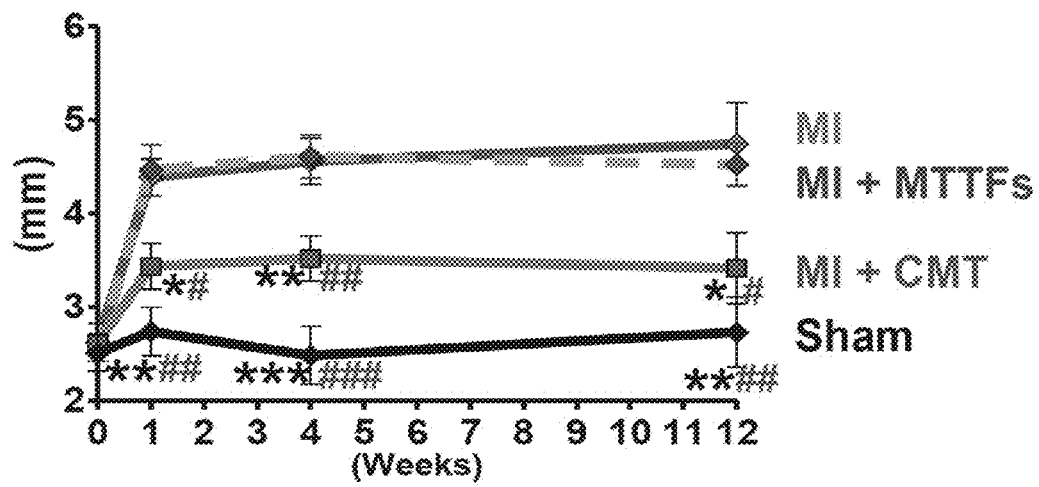
FIG. 3B shows echocardiographic analyses (comparisons of LV end-systolic dimension (LVESD)) before and 1, 4 and 12 weeks after the Transplantation of CMT on MI heart with no injection (MI), MTTFs (MI and MTTF5), CMT (MI and CMT).
Figure 3C:
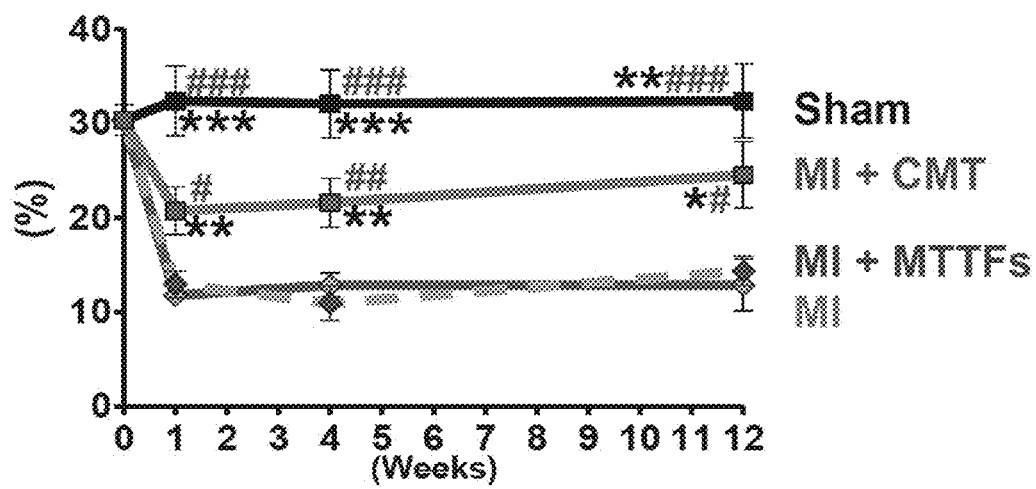
FIG. 3C shows echocardiographic analyses (comparisons of fractional shortening (FS)) before and 1, 4 and 12 weeks after the Transplantation of CMT on MI heart with no injection (MI), MTTFs (MI and MTTF5), CMT (MI and CMT).
Figure 3D:
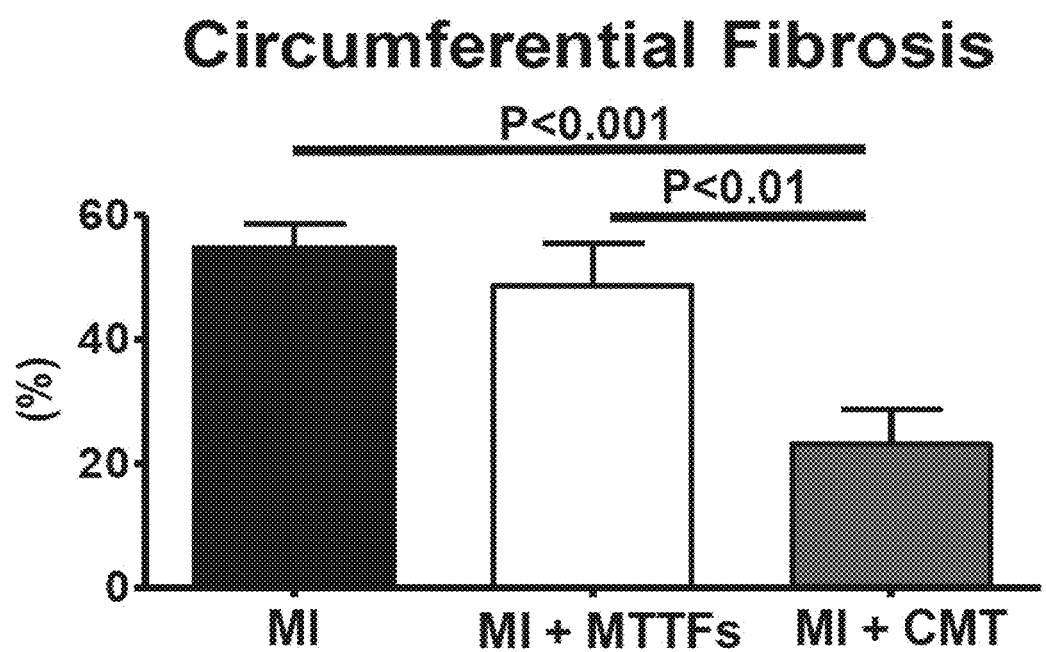
FIG. 3D shows quantitative analyses of the circumferential fibrosis area of cross-sectional pictures of Masson's trichrome stained hearts at the mid (left)- and apical-levels (right) harvested at week 4.

To investigate the therapeutic potential of CMT, CMT were transplanted onto the infarcted mouse heart. Mice were randomly assigned to four groups: Sham, MI without any treatment (MI), MI intramyocardially injected with $5 \times 10^5$ MTTFs (MI+MTTF) and MI transplanted with CMT (MI+CMT) (FIG. 4a). CMTs were generated with GFP-MTTFs at day 10, detached before the surgery, and sutured directly onto the anterior wall and the apex of the heart after ligation of left anterior descending (LAD) coronary artery. Matrix-only control group was not included since the decellularized CMT is semi-solid and not suturable onto the heart and no comparable matrix is commercially available. Echocardiographic analyses showed that LV end-diastolic dimension (LVEDD) and LV end-systolic dimension (LVESD) were smaller, and fractional shortening (FS) was better in the CMT-transplanted MI mice compared to the other two MI groups at weeks 1, 4 and 12 (FIG. 3A-C), demonstrating improved cardiac function in the CMT group. Masson's trichrome staining for 4-week heart samples showed less circumferential fibrosis, cardiac enlargement and wall-thinning in the CMT-transplanted group compared to the other two MI groups (FIG. 3D).

Since the therapeutic effects were observed as early as one week which is before many CMT cells were migrating into the heart side, it was speculated that these effects may not be due to cell generation effects. Thus regional cardiac strains using high-fidelity speckle-tracking imaging in longitudinal axis in the MI and MI+CMT groups 3 and 7 days after the surgery were investigated. Global longitudinal strain (GSL), longitudinal strain of 6 segments (base, mid, and apex of anterior and posterior endocardium) and their time-to-peak to reach the highest strain were calculated using Vevolab software. Abnormal strain patterns such as aberrant magnitude, different direction of wall motion, and heterogeneous time-to-peak shown in the MI group were prevented in the MI+CMT group. GLS ((−)23.4±2.0%) was decreased in both MI and MI+CMT groups at day 3, and further decreased in the MI group but maintained in the MI+CMT group at day 7. Mid-endocardium strain was not distinct but the strain of apex was two-fold higher in MI+CMT group at day 7. These data demonstrate a local contribution of CMT on cardiac strain affecting on the whole cardiac wall motion.

Migration and Engraftment of CMT-Derived Cells

Next, cell engraftment and migration was examined to investigate their contribution to cardiac repair by Masson's trichrome and fluorescence staining. At week 1, GFP-CMT and infarcted heart were clearly distinguishable. Most of GFP+ cells were found in CMT and many GFP-cells were also observed in CMT area suggesting migration of host cells (GFP-but DAPI+) on the CMT side. At week 4, most GFP+-cells migrated into infarcted heart and the CMT size was substantially reduced. Together these data suggest a potential scaffold effects at early (week 1) and cardiac regeneration by CMT at later (≥week 4).

Neovascularization by CMT Transplantation

New vessel formation and neovascularization was examined by the transplanted GFP-CMTs by confocal microscopic examination. Several aspects were considered in the analyses: the contribution of reprogrammed cells in CMT to new vessels as vasculogenesis including coaptation, the contribution of host vessels to new vessels as angiogenesis, and functionality, serial changes, and regional variation (central or border zone) of CMT-derived vessels.

Already at one week, numerous vessels were found on the CMT side which include red blood cells (RBCs), suggesting connection to the systemic circulation. Immunostaining for PECAM1 showed vessel formation by rECs (GFP+PECAM1+) and host ECs (GFP-PECAM1+). These rapidly formed vessels must have supported cell survival in early phase of CMT transplantation. At week 4 in the infarcted area, many GFP+ cells expressed PECAM1 and formed vascular structures, suggesting potent vasculogenesis derived from rECs. Morphologically, rECs (GFP+PECAM1+) formed vascular structures not only by themselves, but also by coaptation with host ECs (GFP-PECAM1+) forming hybrid vessels. In the infarcted area, rECs made up 5.1±0.7% of the total cells and 43.6% of the total GFP+ cells.

To explore the functionality of blood vessels formed by rECs, hearts were perfused with rhodamine-conjugated bandeiraea simplicifolia lectin 1 (BSL1) at week 4. In the infarcted area, numerous BSL1-perfused vessels were seen and many of them were GFP+, indicating their origin from rECs and functional connection to the systemic circulation. GFP-BSL1+ host ECs were observed contributing to formation of various-sized vessels, suggesting strong angiogenesis and maturation. In the border and remote zones, GFP+ cells contributed to neovascularization through vasculogenesis including coaptation.

The contribution of rSMCs/PCs to the formation of vessels was further investigated. Immunostaining for ACTA2 showed ACTA2-expressing GFP+ cells, which surrounded GFP+BSL1+ rEC-derived vessels. These findings indicate that rSMCs contributed to the formation of mature and muscular vessels. GFP-ACTA2+ cells surrounding rEC-derived vessels was also observed, supporting the contribution of host SMCs/PCs to the vessel formation. However, in the GFP-MTTF injected MI hearts, GFP+-cell derived vessels were not detected.

Neovascularization was robustly induced by transplantation of CMT, mRNA expression of angiogenic and cell survival factors including Vegfa, Fgf2, Angpt1, Mmp2, Mmp3, Mmp9, Igf1 and Hgf was examined by qRT-PCR between untreated MI hearts and CMT-transplanted MI hearts at 1 and 4 weeks. At week 1, Mmp3, Igf1 and Hgf levels were higher in CMT-MI hearts compared to the untreated MI hearts. Igf1 and Hgf are cell survival, angiogenic, and cardiomyogenic factors. Three-fold more myocyte were observed in infarcted area in CMT-transplanted heart. At week 4, all examined genes were higher in CMT-MI hearts than untreated MI hearts. Similarly with qRT-PCR results, vessel density examined with PECAM1+ cells clearly demonstrates a significantly higher number of vessels in CMT-transplanted heart at weeks 1 and 4. These data suggest potent paracrine angiogenic and pro-survival effects of CMT.

The vasculature was further examined at week 16 after BSL1 perfusion. In the infarcted area, various-sized vessels consisting of rECs alone, rECs coaptated with host ECs, and host ECs were still observed but most of the rEC-derived vessels were large and tubular, and overall vascularity was reduced. Vessels fully composed of or coaptated with GFP+BSL1+ rECs comprised 21.0±4.2% of the total BSL1+ vessels. Again, ensheathment of rSMCs (GFP+ACTA2+) or host SMCs was observed over rEC-derived tubular vessels. In the border and remote zones, a large number of both hybrid and solely rEC-derived small but not large vessels were observed.

Taken together, these findings demonstrate that CMT-derived rECs and rSMCs/PCs significantly contributed to vessel formation in the central and border zones of infarct hearts through vasculogenesis including coaptation, and induction of angiogenesis through paracrine effects. Over 16 weeks, these reprogrammed cells and CMT-derived vessels underwent dynamic migration and remodeling, forming functional and mature vessels.

Cardiomyogenesis by CMT Transplantation

To investigate whether cardiomyogenesis was induced by CMT transplantation, immunostaining for TNNT2, ACTN2, and GJA1 was conducted with 4 and 16 week samples. At week 4, in the center of the infarct area, GFP+ cells appeared in an aggregated form and many of these GFP+ cells expressed TNNT2 suggesting rCMs. At this time point, rCMs were smaller than host CMs and showed immature sarcomeric organization. GFP+TNNT2+ cells were found in 5.0±0.9% of cells in the infarcted area, accounting for 42.7% of total GFP+ cells. In the border zone, rCMs adjacent to CMs were larger, exhibited organized sarcomeres, and expressed GJA1 between rCMs and host CMs, suggesting mature characteristics of rCMs. At week 16, in the central infarct area, rCMs were rarely observed but in the border zone, more mature rCMs, morphologically indistinguishable from host CMs were observed. These rCMs were polygonal, expressed ACTN2, shared GJA1 molecules with host CMs, and showed clear sarcomeric organization. About 19% of rCMs were bi-nucleated, which was not seen at week 4. Although the number of total rCMs (GFP+ACTN2+) was reduced at this time-point, they comprised 3.7±1.0% of the total ACTN2+ CMs in the border zone.

CMT transplantation into the infarct hearts induced migration of rCMs into the infarcted and the border zones, and allowed them to fully mature over 16 weeks in the border zone and contribute to new CM generation.

Fibroblast Culture and Reprogramming

Mouse tail-tip fibroblasts (MTTFs) isolated from 1-4 month old transgenic mice carrying a GFP reporter driven by αMHC or human ubiquitin C (UBC) promoters were cultured in DMEM/F-12 (Invitrogen) containing 10% FBS (Atlanta Biologicals), 1% Glutamax (Invitrogen), 1% non-essential amino acids (Invitrogen) and 1% Antibiotic-Antimycotic (Invitrogen). αMHC-GFP transgenic mice were kindly given by Dr. Mark Sussman (San Diego State University) and UBC-GFP mice (C57BL/6-Tg(UBC-GFP) 30Scha/J) were purchased from the Jackson Laboratory. After 3-5 passages, MTTFs were frozen until use. MTTFs at 70-80% of confluence were transfected with a synthetic miRNA mimic (20 nM), miR-1a-2-5p (Qiagen, MSY0017047, 5'-ACAUACUUCUUUAUGUAGUAC-CCAUA-3')(SEQ ID NO: 135), miR-208a-3p (Qiagen, MSY0000520, 5'-AUAAGACGAGCAAAAAGCUUGU-3')(SEQ ID NO: 136), miR-208b-3p (Qiagen, MSY0004939, 5'-AUAAGACGAACAAAAGGUUUGU-3')(SEQ ID NO: 1), miR-208b-5p (Qiagen, MSY0017280, 5'-AAGCUUUUUGCUCGCGUUAUGU-3')(SEQ ID NO: 137), miR-499-5p (Qiagen, MSY0003482, 5'-UUAAGAC-UUGCAGUGAUGUUU-3') (SEQ ID NO: 3) or Scramble-miR (Dharmacon, CN-001000-01-05) using Lipofectamine 2000 (Invitrogen), and cultured in advanced DMEM/F12 (Invitrogen) containing 5% FBS (Atlanta Biologicals), 0.5% Glutamax (Invitrogen), 0.5% non-essential amino acids and 1% Antibiotic-Antimycotic (Invitrogen) with or without AA (ascorbic acid, Sigma, 0.2 mM) and BMP4 (R&D Systems, 10 ng/ml) for fibroblast reprogramming. Cells on a culture dish spontaneously aggregated as a patch-like CMT on day 10. In the case of no spontaneous formation, the border of a culture dish was scratched and cells were lifted up with a pipette to expedite cell aggregation into a CMT.

The invention claimed is:

1. A method of making cardio-mimetic tissue by mixing fibroblast cells with ascorbic acid and bone morphogenetic protein 4 and inserting into the fibroblast cells a nucleobase polymer with a nucleotide sequence consisting of or comprising a sequence selected from AUAAGACGAACAAAAGGUUUGU (SEQ ID NO: 1), or variant with 65% or greater identity thereto, and under conditions such that a tissue is formed that is capable of spontaneously contracting.

2. The method of claim 1, wherein the cells are human dermal fibroblasts.

3. The method of claim 1, wherein inserting the nucleobase polymer is done by mixing the nucleobase polymer in the presence a cationic lipid and exposing the mixture to a fibroblast cell or by incorporating the nucleotide sequence in a viral nucleic acid or particle, plasmid, or other vector.

4. The method of claim 1, wherein the cardio-mimetic tissue comprises cells that have an increased expression of mRNA Myh6 when compared to cells mixed with ascorbic acid and bone morphogenetic protein 4 in the absence of the nucleobase polymer.

5. The method of claim 1, wherein the cardio-mimetic tissue comprises cells have increased expression of TNNT2 when compared to cells mixed with ascorbic acid and bone morphogenetic protein 4 in the absence of the nucleobase polymer.

6. The method of claim 1, wherein the variant of SEQ ID NO: 1 has one, two, three, four, five, six, or seven nucleotide substitutions, deletions, or combinations thereof.

7. The method of claim 1, wherein the variant of SEQ ID NO: 1 comprises the sequence UAAGACXXXCA-(X)$_n$AXGCUU (SEQ ID NO: 2) wherein n is 2 or 3, U is individually and independently uracil or thymine, and X is individually at each occurrence any nucleotide.

8. A method of treating heart disease comprising,
isolating fibroblast cells from a subject diagnosed with heart disease thereby providing isolated fibroblast cells;
making cardio-mimetic tissue capable of spontaneously contracting by the process of inserting or expressing inside the isolated fibroblast cells a nucleobase polymer comprising a nucleotide sequence consisting of or comprising AUAAGACGAACAAAAGGUUUGU (SEQ ID NO: 1), or variant with 65% or greater identity thereto, and then contacting the isolated fibroblast cells with ascorbic acid and bone morphogenetic protein 4 under conditions such that a tissue capable of spontaneously contracting is formed thereby providing a cardiomimetic tissue; and
implanting the cardio-mimetic tissue effectively on or in the heart of the subject.

9. The method of claim 8, wherein the cells are fibroblasts or human dermal fibroblasts.

10. The method of claim 8, wherein inserting the nucleobase polymer is done by mixing the nucleobase polymer in the presence a cationic lipid and exposing the mixture to a fibroblast cell or by incorporating the nucleotide sequence in a viral nucleic acid or particle, plasmid, or other vector.

11. A method of treating heart disease comprising administering an effective amount of ascorbic acid or prodrug thereof and bone morphogenetic protein 4 in combination with an expression vector encoding a nucleobase polymer comprising sequence AUAAGACGAACAAAAGGUUUGU SEQ ID NO: 1 or variant with 65% or greater identity thereto, to a subject in need thereof, wherein administration is by injection into a peritoneal cavity or heart of the subject.

12. The method of claim 11, wherein the subject is a human.

13. The method of claim 11, wherein bone morphogenetic protein 4 is a human isoform.

14. The method of claim 11, wherein the subject is diagnosed with a myocardial infarction.

* * * * *

SEQUENCE LISTING

<160> NUMBER OF SEQ ID NOS: 138

<210> SEQ ID NO 1
<211> LENGTH: 22
<212> TYPE: RNA
<213> ORGANISM: Mus musculus

<400> SEQUENCE: 1

```
auaagacgaa caaaagguuu gu                                              22

<210> SEQ ID NO 2
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: n
<222> LOCATION: (1)..(20)
<223> OTHER INFORMATION: n is individually at each occurance any
      nucleotide
<220> FEATURE:
<221> NAME/KEY: misc_feature
<222> LOCATION: (7)..(9)
<223> OTHER INFORMATION: n is a, c, g, t or u
<220> FEATURE:
<221> NAME/KEY: misc_feature
<222> LOCATION: (12)..(14)
<223> OTHER INFORMATION: n is a, c, g, t or u
<220> FEATURE:
<221> NAME/KEY: misc_feature
<222> LOCATION: (16)..(16)
<223> OTHER INFORMATION: n is a, c, g, t or u

<400> SEQUENCE: 2
uaagacnnnc annnangcuu                                                 20

<210> SEQ ID NO 3
<211> LENGTH: 21
<212> TYPE: RNA
<213> ORGANISM: Mus musculus

<400> SEQUENCE: 3
uuaagacuug cagugauguu u                                               21

<210> SEQ ID NO 4
<211> LENGTH: 21
<212> TYPE: DNA
<213> ORGANISM: Artificial
<220> FEATURE:
<223> OTHER INFORMATION: Synthetic

<400> SEQUENCE: 4
auaagacgaa caaaagguuu g                                               21

<210> SEQ ID NO 5
<211> LENGTH: 19
<212> TYPE: DNA
<213> ORGANISM: Artificial
<220> FEATURE:
<223> OTHER INFORMATION: Synthetic

<400> SEQUENCE: 5
auaagacgaa caaaagguu                                                  19

<210> SEQ ID NO 6
<211> LENGTH: 18
<212> TYPE: DNA
<213> ORGANISM: Artificial
<220> FEATURE:
<223> OTHER INFORMATION: Synthetic

<400> SEQUENCE: 6
auaagacgaa caaaaggu                                                   18
```

```
<210> SEQ ID NO 7
<211> LENGTH: 17
<212> TYPE: DNA
<213> ORGANISM: Artificial
<220> FEATURE:
<223> OTHER INFORMATION: Synthetic

<400> SEQUENCE: 7
auaagacgaa caaaagg                                                    17

<210> SEQ ID NO 8
<211> LENGTH: 21
<212> TYPE: DNA
<213> ORGANISM: Artificial
<220> FEATURE:
<223> OTHER INFORMATION: Synthetic

<400> SEQUENCE: 8
uaagacgaac aaaagguuug u                                               21

<210> SEQ ID NO 9
<211> LENGTH: 20
<212> TYPE: DNA
<213> ORGANISM: Artificial
<220> FEATURE:
<223> OTHER INFORMATION: Synthetic

<400> SEQUENCE: 9
aagacgaaca aaagguuugu                                                 20

<210> SEQ ID NO 10
<211> LENGTH: 19
<212> TYPE: DNA
<213> ORGANISM: Artificial
<220> FEATURE:
<223> OTHER INFORMATION: Synthetic

<400> SEQUENCE: 10
agacgaacaa aagguuugu                                                  19

<210> SEQ ID NO 11
<211> LENGTH: 18
<212> TYPE: DNA
<213> ORGANISM: Artificial
<220> FEATURE:
<223> OTHER INFORMATION: Synthetic

<400> SEQUENCE: 11
gacgaacaaa agguuugu                                                   18

<210> SEQ ID NO 12
<211> LENGTH: 17
<212> TYPE: DNA
<213> ORGANISM: Artificial
<220> FEATURE:
<223> OTHER INFORMATION: Synthetic

<400> SEQUENCE: 12
acgaacaaaa gguuugu                                                    17

<210> SEQ ID NO 13
<211> LENGTH: 20
<212> TYPE: DNA
<213> ORGANISM: Artificial
<220> FEATURE:
<223> OTHER INFORMATION: Synthetic
```

```
<400> SEQUENCE: 13
uaagacgaac aaaagguuug                                               20

<210> SEQ ID NO 14
<211> LENGTH: 19
<212> TYPE: DNA
<213> ORGANISM: Artificial
<220> FEATURE:
<223> OTHER INFORMATION: Synthetic

<400> SEQUENCE: 14
uaagacgaac aaaagguuu                                                19

<210> SEQ ID NO 15
<211> LENGTH: 18
<212> TYPE: DNA
<213> ORGANISM: Artificial
<220> FEATURE:
<223> OTHER INFORMATION: Synthetic

<400> SEQUENCE: 15
uaagacgaac aaaagguu                                                 18

<210> SEQ ID NO 16
<211> LENGTH: 17
<212> TYPE: DNA
<213> ORGANISM: Artificial
<220> FEATURE:
<223> OTHER INFORMATION: Synthetic

<400> SEQUENCE: 16
uaagacgaac aaaaggu                                                  17

<210> SEQ ID NO 17
<211> LENGTH: 18
<212> TYPE: DNA
<213> ORGANISM: Artificial
<220> FEATURE:
<223> OTHER INFORMATION: Synthetic

<400> SEQUENCE: 17
aagacgaaca aaagguuu                                                 18

<210> SEQ ID NO 18
<211> LENGTH: 17
<212> TYPE: DNA
<213> ORGANISM: Artificial
<220> FEATURE:
<223> OTHER INFORMATION: Synthetic

<400> SEQUENCE: 18
aagacgaaca aaagguu                                                  17

<210> SEQ ID NO 19
<211> LENGTH: 18
<212> TYPE: DNA
<213> ORGANISM: Artificial
<220> FEATURE:
<223> OTHER INFORMATION: Synthetic

<400> SEQUENCE: 19
agacgaacaa aagguuug                                                 18

<210> SEQ ID NO 20
<211> LENGTH: 17
```

```
<212> TYPE: DNA
<213> ORGANISM: Artificial
<220> FEATURE:
<223> OTHER INFORMATION: Synthetic

<400> SEQUENCE: 20
agacgaacaa aagguuu                                                    17

<210> SEQ ID NO 21
<211> LENGTH: 17
<212> TYPE: DNA
<213> ORGANISM: Artificial
<220> FEATURE:
<223> OTHER INFORMATION: Synthetic

<400> SEQUENCE: 21
gacgaacaaa agguuug                                                    17

<210> SEQ ID NO 22
<211> LENGTH: 21
<212> TYPE: DNA
<213> ORGANISM: Artificial
<220> FEATURE:
<223> OTHER INFORMATION: Synthetic

<400> SEQUENCE: 22
auaagacuaa caaaagguuu g                                               21

<210> SEQ ID NO 23
<211> LENGTH: 20
<212> TYPE: DNA
<213> ORGANISM: Artificial
<220> FEATURE:
<223> OTHER INFORMATION: Synthetic

<400> SEQUENCE: 23
auaagacuaa caaaagguuu                                                 20

<210> SEQ ID NO 24
<211> LENGTH: 19
<212> TYPE: DNA
<213> ORGANISM: Artificial
<220> FEATURE:
<223> OTHER INFORMATION: Synthetic

<400> SEQUENCE: 24
auaagacuaa caaaagguu                                                  19

<210> SEQ ID NO 25
<211> LENGTH: 18
<212> TYPE: DNA
<213> ORGANISM: Artificial
<220> FEATURE:
<223> OTHER INFORMATION: Synthetic

<400> SEQUENCE: 25
auaagacuaa caaaaggu                                                   18

<210> SEQ ID NO 26
<211> LENGTH: 17
<212> TYPE: DNA
<213> ORGANISM: Artificial
<220> FEATURE:
<223> OTHER INFORMATION: Synthetic

<400> SEQUENCE: 26
```

-continued

```
auaagacuaa caaaagg                                              17

<210> SEQ ID NO 27
<211> LENGTH: 21
<212> TYPE: DNA
<213> ORGANISM: Artificial
<220> FEATURE:
<223> OTHER INFORMATION: Synthetic

<400> SEQUENCE: 27
uaagacuaac aaaagguuug u                                         21

<210> SEQ ID NO 28
<211> LENGTH: 20
<212> TYPE: DNA
<213> ORGANISM: Artificial
<220> FEATURE:
<223> OTHER INFORMATION: Synthetic

<400> SEQUENCE: 28
aagacuaaca aaagguuugu                                           20

<210> SEQ ID NO 29
<211> LENGTH: 19
<212> TYPE: DNA
<213> ORGANISM: Artificial
<220> FEATURE:
<223> OTHER INFORMATION: Synthetic

<400> SEQUENCE: 29
agacuaacaa aagguuugu                                            19

<210> SEQ ID NO 30
<211> LENGTH: 18
<212> TYPE: DNA
<213> ORGANISM: Artificial
<220> FEATURE:
<223> OTHER INFORMATION: Synthetic

<400> SEQUENCE: 30
gacuaacaaa agguuugu                                             18

<210> SEQ ID NO 31
<211> LENGTH: 17
<212> TYPE: DNA
<213> ORGANISM: Artificial
<220> FEATURE:
<223> OTHER INFORMATION: Synthetic

<400> SEQUENCE: 31
acuaacaaaa gguuugu                                              17

<210> SEQ ID NO 32
<211> LENGTH: 20
<212> TYPE: DNA
<213> ORGANISM: Artificial
<220> FEATURE:
<223> OTHER INFORMATION: Synthetic

<400> SEQUENCE: 32
uaagacuaac aaaagguuug                                           20

<210> SEQ ID NO 33
<211> LENGTH: 19
<212> TYPE: DNA
<213> ORGANISM: Artificial
```

```
<220> FEATURE:
<223> OTHER INFORMATION: Synthetic

<400> SEQUENCE: 33
uaagacuaac aaaagguuu                                              19

<210> SEQ ID NO 34
<211> LENGTH: 18
<212> TYPE: DNA
<213> ORGANISM: Artificial
<220> FEATURE:
<223> OTHER INFORMATION: Synthetic

<400> SEQUENCE: 34
uaagacuaac aaaagguu                                               18

<210> SEQ ID NO 35
<211> LENGTH: 17
<212> TYPE: DNA
<213> ORGANISM: Artificial
<220> FEATURE:
<223> OTHER INFORMATION: Synthetic

<400> SEQUENCE: 35
uaagacuaac aaaaggu                                                17

<210> SEQ ID NO 36
<211> LENGTH: 18
<212> TYPE: DNA
<213> ORGANISM: Artificial
<220> FEATURE:
<223> OTHER INFORMATION: Synthetic

<400> SEQUENCE: 36
aagacuaaca aaagguuu                                               18

<210> SEQ ID NO 37
<211> LENGTH: 17
<212> TYPE: DNA
<213> ORGANISM: Artificial
<220> FEATURE:
<223> OTHER INFORMATION: Synthetic

<400> SEQUENCE: 37
aagacuaaca aaagguu                                                17

<210> SEQ ID NO 38
<211> LENGTH: 18
<212> TYPE: DNA
<213> ORGANISM: Artificial
<220> FEATURE:
<223> OTHER INFORMATION: Synthetic

<400> SEQUENCE: 38
agacuaacaa aagguuug                                               18

<210> SEQ ID NO 39
<211> LENGTH: 17
<212> TYPE: DNA
<213> ORGANISM: Artificial
<220> FEATURE:
<223> OTHER INFORMATION: Synthetic

<400> SEQUENCE: 39
agacuaacaa aagguuu                                                17
```

```
<210> SEQ ID NO 40
<211> LENGTH: 17
<212> TYPE: DNA
<213> ORGANISM: Artificial
<220> FEATURE:
<223> OTHER INFORMATION: Synthetic

<400> SEQUENCE: 40
gacuaacaaa agguuug                                                   17

<210> SEQ ID NO 41
<211> LENGTH: 21
<212> TYPE: DNA
<213> ORGANISM: Artificial
<220> FEATURE:
<223> OTHER INFORMATION: Synthetic

<400> SEQUENCE: 41
auaagacuua caaaagguuu g                                              21

<210> SEQ ID NO 42
<211> LENGTH: 20
<212> TYPE: DNA
<213> ORGANISM: Artificial
<220> FEATURE:
<223> OTHER INFORMATION: Synthetic

<400> SEQUENCE: 42
auaagacuua caaaagguuu                                                20

<210> SEQ ID NO 43
<211> LENGTH: 19
<212> TYPE: DNA
<213> ORGANISM: Artificial
<220> FEATURE:
<223> OTHER INFORMATION: Synthetic

<400> SEQUENCE: 43
auaagacuua caaaagguu                                                 19

<210> SEQ ID NO 44
<211> LENGTH: 18
<212> TYPE: DNA
<213> ORGANISM: Artificial
<220> FEATURE:
<223> OTHER INFORMATION: Synthetic

<400> SEQUENCE: 44
auaagacuua caaaaggu                                                  18

<210> SEQ ID NO 45
<211> LENGTH: 17
<212> TYPE: DNA
<213> ORGANISM: Artificial
<220> FEATURE:
<223> OTHER INFORMATION: Synthetic

<400> SEQUENCE: 45
auaagacuua caaaagg                                                   17

<210> SEQ ID NO 46
<211> LENGTH: 21
<212> TYPE: DNA
<213> ORGANISM: Artificial
<220> FEATURE:
<223> OTHER INFORMATION: Synthetic
```

<400> SEQUENCE: 46
uaagacuuac aaaagguuug u                                            21

<210> SEQ ID NO 47
<211> LENGTH: 20
<212> TYPE: DNA
<213> ORGANISM: Artificial
<220> FEATURE:
<223> OTHER INFORMATION: Synthetic

<400> SEQUENCE: 47
aagacuuaca aaagguuugu                                              20

<210> SEQ ID NO 48
<211> LENGTH: 19
<212> TYPE: DNA
<213> ORGANISM: Artificial
<220> FEATURE:
<223> OTHER INFORMATION: Synthetic

<400> SEQUENCE: 48
agacuuacaa aagguuugu                                               19

<210> SEQ ID NO 49
<211> LENGTH: 18
<212> TYPE: DNA
<213> ORGANISM: Artificial
<220> FEATURE:
<223> OTHER INFORMATION: Synthetic

<400> SEQUENCE: 49
gacuuacaaa agguuugu                                                18

<210> SEQ ID NO 50
<211> LENGTH: 17
<212> TYPE: DNA
<213> ORGANISM: Artificial
<220> FEATURE:
<223> OTHER INFORMATION: Synthetic

<400> SEQUENCE: 50
acuuacaaaa gguuugu                                                 17

<210> SEQ ID NO 51
<211> LENGTH: 20
<212> TYPE: DNA
<213> ORGANISM: Artificial
<220> FEATURE:
<223> OTHER INFORMATION: Synthetic

<400> SEQUENCE: 51
uaagacuuac aaaagguuug                                              20

<210> SEQ ID NO 52
<211> LENGTH: 19
<212> TYPE: DNA
<213> ORGANISM: Artificial
<220> FEATURE:
<223> OTHER INFORMATION: Synthetic

<400> SEQUENCE: 52
uaagacuuac aaaagguuu                                               19

<210> SEQ ID NO 53

```
<211> LENGTH: 18
<212> TYPE: DNA
<213> ORGANISM: Artificial
<220> FEATURE:
<223> OTHER INFORMATION: Synthetic

<400> SEQUENCE: 53
uaagacuuac aaaagguu                                                 18

<210> SEQ ID NO 54
<211> LENGTH: 17
<212> TYPE: DNA
<213> ORGANISM: Artificial
<220> FEATURE:
<223> OTHER INFORMATION: Synthetic

<400> SEQUENCE: 54
uaagacuuac aaaaggu                                                  17

<210> SEQ ID NO 55
<211> LENGTH: 18
<212> TYPE: DNA
<213> ORGANISM: Artificial
<220> FEATURE:
<223> OTHER INFORMATION: Synthetic

<400> SEQUENCE: 55
aagacuuaca aaagguuu                                                 18

<210> SEQ ID NO 56
<211> LENGTH: 17
<212> TYPE: DNA
<213> ORGANISM: Artificial
<220> FEATURE:
<223> OTHER INFORMATION: Synthetic

<400> SEQUENCE: 56
aagacuuaca aaagguu                                                  17

<210> SEQ ID NO 57
<211> LENGTH: 18
<212> TYPE: DNA
<213> ORGANISM: Artificial
<220> FEATURE:
<223> OTHER INFORMATION: Synthetic

<400> SEQUENCE: 57
agacuuacaa aagguuug                                                 18

<210> SEQ ID NO 58
<211> LENGTH: 17
<212> TYPE: DNA
<213> ORGANISM: Artificial
<220> FEATURE:
<223> OTHER INFORMATION: Synthetic

<400> SEQUENCE: 58
agacuuacaa aagguuu                                                  17

<210> SEQ ID NO 59
<211> LENGTH: 17
<212> TYPE: DNA
<213> ORGANISM: Artificial
<220> FEATURE:
<223> OTHER INFORMATION: Synthetic

<400> SEQUENCE: 59
```

-continued gacuuacaaa agguuug                                                17

<210> SEQ ID NO 60
<211> LENGTH: 21
<212> TYPE: DNA
<213> ORGANISM: Artificial
<220> FEATURE:
<223> OTHER INFORMATION: Synthetic

<400> SEQUENCE: 60
auaagacgag caaaagguuu g                                           21

<210> SEQ ID NO 61
<211> LENGTH: 20
<212> TYPE: DNA
<213> ORGANISM: Artificial
<220> FEATURE:
<223> OTHER INFORMATION: Synthetic

<400> SEQUENCE: 61
auaagacgag caaaagguuu                                             20

<210> SEQ ID NO 62
<211> LENGTH: 19
<212> TYPE: DNA
<213> ORGANISM: Artificial
<220> FEATURE:
<223> OTHER INFORMATION: Synthetic

<400> SEQUENCE: 62
auaagacgag caaaagguu                                              19

<210> SEQ ID NO 63
<211> LENGTH: 18
<212> TYPE: DNA
<213> ORGANISM: Artificial
<220> FEATURE:
<223> OTHER INFORMATION: Synthetic

<400> SEQUENCE: 63
auaagacgag caaaaggu                                               18

<210> SEQ ID NO 64
<211> LENGTH: 17
<212> TYPE: DNA
<213> ORGANISM: Artificial
<220> FEATURE:
<223> OTHER INFORMATION: Synthetic

<400> SEQUENCE: 64
auaagacgag caaaagg                                                17

<210> SEQ ID NO 65
<211> LENGTH: 21
<212> TYPE: DNA
<213> ORGANISM: Artificial
<220> FEATURE:
<223> OTHER INFORMATION: Synthetic

<400> SEQUENCE: 65
uaagacgagc aaaagguuug u                                           21

<210> SEQ ID NO 66
<211> LENGTH: 20
<212> TYPE: DNA

```
<213> ORGANISM: Artificial
<220> FEATURE:
<223> OTHER INFORMATION: Synthetic

<400> SEQUENCE: 66
aagacgagca aaagguuugu                                           20

<210> SEQ ID NO 67
<211> LENGTH: 6
<212> TYPE: DNA
<213> ORGANISM: Artificial
<220> FEATURE:
<223> OTHER INFORMATION: Synthetic

<400> SEQUENCE: 67 cccccc                                                           6

<210> SEQ ID NO 68
<211> LENGTH: 5
<212> TYPE: DNA
<213> ORGANISM: Artificial
<220> FEATURE:
<223> OTHER INFORMATION: Synthetic

<400> SEQUENCE: 68 ccacc                                                            5

<210> SEQ ID NO 69
<211> LENGTH: 6
<212> TYPE: DNA
<213> ORGANISM: Artificial
<220> FEATURE:
<223> OTHER INFORMATION: Synthetic

<400> SEQUENCE: 69 cccttt                                                           6

<210> SEQ ID NO 70
<211> LENGTH: 19
<212> TYPE: DNA
<213> ORGANISM: Artificial
<220> FEATURE:
<223> OTHER INFORMATION: Synthetic

<400> SEQUENCE: 70
agacgagcaa aagguuugu                                            19

<210> SEQ ID NO 71
<211> LENGTH: 18
<212> TYPE: DNA
<213> ORGANISM: Artificial
<220> FEATURE:
<223> OTHER INFORMATION: Synthetic

<400> SEQUENCE: 71
gacgagcaaa agguuugu                                             18

<210> SEQ ID NO 72
<211> LENGTH: 17
<212> TYPE: DNA
<213> ORGANISM: Artificial
<220> FEATURE:
<223> OTHER INFORMATION: Synthetic

<400> SEQUENCE: 72
acgagcaaaa gguuugu                                              17
```

<210> SEQ ID NO 73
<211> LENGTH: 20
<212> TYPE: DNA
<213> ORGANISM: Artificial
<220> FEATURE:
<223> OTHER INFORMATION: Synthetic

<400> SEQUENCE: 73
uaagacgagc aaaagguuug					20

<210> SEQ ID NO 74
<211> LENGTH: 19
<212> TYPE: DNA
<213> ORGANISM: Artificial
<220> FEATURE:
<223> OTHER INFORMATION: Synthetic

<400> SEQUENCE: 74
uaagacgagc aaaagguuu					19

<210> SEQ ID NO 75
<211> LENGTH: 18
<212> TYPE: DNA
<213> ORGANISM: Artificial
<220> FEATURE:
<223> OTHER INFORMATION: Synthetic

<400> SEQUENCE: 75
uaagacgagc aaaagguu					18

<210> SEQ ID NO 76
<211> LENGTH: 17
<212> TYPE: DNA
<213> ORGANISM: Artificial
<220> FEATURE:
<223> OTHER INFORMATION: Synthetic

<400> SEQUENCE: 76
uaagacgagc aaaaggu					17

<210> SEQ ID NO 77
<211> LENGTH: 18
<212> TYPE: DNA
<213> ORGANISM: Artificial
<220> FEATURE:
<223> OTHER INFORMATION: Synthetic

<400> SEQUENCE: 77
aagacgagca aaagguuu					18

<210> SEQ ID NO 78
<211> LENGTH: 17
<212> TYPE: DNA
<213> ORGANISM: Artificial
<220> FEATURE:
<223> OTHER INFORMATION: Synthetic

<400> SEQUENCE: 78
aagacgagca aaagguu					17

<210> SEQ ID NO 79
<211> LENGTH: 18
<212> TYPE: DNA
<213> ORGANISM: Artificial
<220> FEATURE:

```
<223> OTHER INFORMATION: Synthetic

<400> SEQUENCE: 79
agacgagcaa aagguuug                                                 18

<210> SEQ ID NO 80
<211> LENGTH: 17
<212> TYPE: DNA
<213> ORGANISM: Artificial
<220> FEATURE:
<223> OTHER INFORMATION: Synthetic

<400> SEQUENCE: 80
agacgagcaa aagguuu                                                  17

<210> SEQ ID NO 81
<211> LENGTH: 17
<212> TYPE: DNA
<213> ORGANISM: Artificial
<220> FEATURE:
<223> OTHER INFORMATION: Synthetic

<400> SEQUENCE: 81
gacgagcaaa agguuug                                                  17

<210> SEQ ID NO 82
<211> LENGTH: 21
<212> TYPE: DNA
<213> ORGANISM: Artificial
<220> FEATURE:
<223> OTHER INFORMATION: Synthetic

<400> SEQUENCE: 82
auaagacgaa cagaagguuu g                                             21

<210> SEQ ID NO 83
<211> LENGTH: 20
<212> TYPE: DNA
<213> ORGANISM: Artificial
<220> FEATURE:
<223> OTHER INFORMATION: Synthetic

<400> SEQUENCE: 83
auaagacgaa cagaagguuu                                               20

<210> SEQ ID NO 84
<211> LENGTH: 19
<212> TYPE: DNA
<213> ORGANISM: Artificial
<220> FEATURE:
<223> OTHER INFORMATION: Synthetic

<400> SEQUENCE: 84
auaagacgaa cagaagguu                                                19

<210> SEQ ID NO 85
<211> LENGTH: 18
<212> TYPE: DNA
<213> ORGANISM: Artificial
<220> FEATURE:
<223> OTHER INFORMATION: Synthetic

<400> SEQUENCE: 85
auaagacgaa cagaaggu                                                 18
```

<210> SEQ ID NO 86
<211> LENGTH: 17
<212> TYPE: DNA
<213> ORGANISM: Artificial
<220> FEATURE:
<223> OTHER INFORMATION: Synthetic

<400> SEQUENCE: 86
auaagacgaa cagaagg                                                17

<210> SEQ ID NO 87
<211> LENGTH: 21
<212> TYPE: DNA
<213> ORGANISM: Artificial
<220> FEATURE:
<223> OTHER INFORMATION: Synthetic

<400> SEQUENCE: 87
uaagacgaac agaagguuug u                                           21

<210> SEQ ID NO 88
<211> LENGTH: 20
<212> TYPE: DNA
<213> ORGANISM: Artificial
<220> FEATURE:
<223> OTHER INFORMATION: Synthetic

<400> SEQUENCE: 88
aagacgaaca gaagguuugu                                             20

<210> SEQ ID NO 89
<211> LENGTH: 19
<212> TYPE: DNA
<213> ORGANISM: Artificial
<220> FEATURE:
<223> OTHER INFORMATION: Synthetic

<400> SEQUENCE: 89
agacgaacag aagguuugu                                              19

<210> SEQ ID NO 90
<211> LENGTH: 18
<212> TYPE: DNA
<213> ORGANISM: Artificial
<220> FEATURE:
<223> OTHER INFORMATION: Synthetic

<400> SEQUENCE: 90
gacgaacaga agguuugu                                               18

<210> SEQ ID NO 91
<211> LENGTH: 17
<212> TYPE: DNA
<213> ORGANISM: Artificial
<220> FEATURE:
<223> OTHER INFORMATION: Synthetic

<400> SEQUENCE: 91
acgaacagaa gguuugu                                                17

<210> SEQ ID NO 92
<211> LENGTH: 20
<212> TYPE: DNA
<213> ORGANISM: Artificial
<220> FEATURE:
<223> OTHER INFORMATION: Synthetic

```
<400> SEQUENCE: 92
uaagacgaac agaagguuug                                              20

<210> SEQ ID NO 93
<211> LENGTH: 19
<212> TYPE: DNA
<213> ORGANISM: Artificial
<220> FEATURE:
<223> OTHER INFORMATION: Synthetic

<400> SEQUENCE: 93
uaagacgaac agaagguuu                                               19

<210> SEQ ID NO 94
<211> LENGTH: 18
<212> TYPE: DNA
<213> ORGANISM: Artificial
<220> FEATURE:
<223> OTHER INFORMATION: Synthetic

<400> SEQUENCE: 94
uaagacgaac agaagguu                                                18

<210> SEQ ID NO 95
<211> LENGTH: 17
<212> TYPE: DNA
<213> ORGANISM: Artificial
<220> FEATURE:
<223> OTHER INFORMATION: Synthetic

<400> SEQUENCE: 95
uaagacgaac agaaggu                                                 17

<210> SEQ ID NO 96
<211> LENGTH: 18
<212> TYPE: DNA
<213> ORGANISM: Artificial
<220> FEATURE:
<223> OTHER INFORMATION: Synthetic

<400> SEQUENCE: 96
aagacgaaca gaagguuu                                                18

<210> SEQ ID NO 97
<211> LENGTH: 17
<212> TYPE: DNA
<213> ORGANISM: Artificial
<220> FEATURE:
<223> OTHER INFORMATION: Synthetic

<400> SEQUENCE: 97
aagacgaaca gaagguu                                                 17

<210> SEQ ID NO 98
<211> LENGTH: 18
<212> TYPE: DNA
<213> ORGANISM: Artificial
<220> FEATURE:
<223> OTHER INFORMATION: Synthetic

<400> SEQUENCE: 98
agacgaacag aagguuug                                                18

<210> SEQ ID NO 99
<211> LENGTH: 17
```

```
<212> TYPE: DNA
<213> ORGANISM: Artificial
<220> FEATURE:
<223> OTHER INFORMATION: Synthetic

<400> SEQUENCE: 99
agacgaacag aagguuu                                                    17

<210> SEQ ID NO 100
<211> LENGTH: 17
<212> TYPE: DNA
<213> ORGANISM: Artificial
<220> FEATURE:
<223> OTHER INFORMATION: Synthetic

<400> SEQUENCE: 100
gacgaacaga agguuug                                                    17

<210> SEQ ID NO 101
<211> LENGTH: 21
<212> TYPE: DNA
<213> ORGANISM: Artificial
<220> FEATURE:
<223> OTHER INFORMATION: Synthetic

<400> SEQUENCE: 101
auaagacgaa caguagguuu g                                               21

<210> SEQ ID NO 102
<211> LENGTH: 20
<212> TYPE: DNA
<213> ORGANISM: Artificial
<220> FEATURE:
<223> OTHER INFORMATION: Synthetic

<400> SEQUENCE: 102
auaagacgaa caguagguuu                                                 20

<210> SEQ ID NO 103
<211> LENGTH: 19
<212> TYPE: DNA
<213> ORGANISM: Artificial
<220> FEATURE:
<223> OTHER INFORMATION: Synthetic

<400> SEQUENCE: 103
auaagacgaa caguagguu                                                  19

<210> SEQ ID NO 104
<211> LENGTH: 18
<212> TYPE: DNA
<213> ORGANISM: Artificial
<220> FEATURE:
<223> OTHER INFORMATION: Synthetic

<400> SEQUENCE: 104
auaagacgaa caguaggu                                                   18

<210> SEQ ID NO 105
<211> LENGTH: 17
<212> TYPE: DNA
<213> ORGANISM: Artificial
<220> FEATURE:
<223> OTHER INFORMATION: Synthetic

<400> SEQUENCE: 105
```
auaagacgaa caguagg                                                     17

<210> SEQ ID NO 106
<211> LENGTH: 21
<212> TYPE: DNA
<213> ORGANISM: Artificial
<220> FEATURE:
<223> OTHER INFORMATION: Synthetic

<400> SEQUENCE: 106
uaagacgaac aguagguuug u                                                21

<210> SEQ ID NO 107
<211> LENGTH: 20
<212> TYPE: DNA
<213> ORGANISM: Artificial
<220> FEATURE:
<223> OTHER INFORMATION: Synthetic

<400> SEQUENCE: 107
aagacgaaca guagguuugu                                                  20

<210> SEQ ID NO 108
<211> LENGTH: 19
<212> TYPE: DNA
<213> ORGANISM: Artificial
<220> FEATURE:
<223> OTHER INFORMATION: Synthetic

<400> SEQUENCE: 108
agacgaacag uagguuugu                                                   19

<210> SEQ ID NO 109
<211> LENGTH: 18
<212> TYPE: DNA
<213> ORGANISM: Artificial
<220> FEATURE:
<223> OTHER INFORMATION: Synthetic

<400> SEQUENCE: 109
gacgaacagu agguuugu                                                    18

<210> SEQ ID NO 110
<211> LENGTH: 7
<212> TYPE: DNA
<213> ORGANISM: Artificial
<220> FEATURE:
<223> OTHER INFORMATION: Synthetic

<400> SEQUENCE: 110 cccattt                                                                 7

<210> SEQ ID NO 111
<211> LENGTH: 17
<212> TYPE: DNA
<213> ORGANISM: Artificial
<220> FEATURE:
<223> OTHER INFORMATION: Synthetic

<400> SEQUENCE: 111
acgaacagua gguuugu                                                     17

<210> SEQ ID NO 112
<211> LENGTH: 20
<212> TYPE: DNA
<213> ORGANISM: Artificial

```
<220> FEATURE:
<223> OTHER INFORMATION: Synthetic

<400> SEQUENCE: 112
uaagacgaac aguagguuug                                              20

<210> SEQ ID NO 113
<211> LENGTH: 19
<212> TYPE: DNA
<213> ORGANISM: Artificial
<220> FEATURE:
<223> OTHER INFORMATION: Synthetic

<400> SEQUENCE: 113
uaagacgaac aguagguuu                                               19

<210> SEQ ID NO 114
<211> LENGTH: 18
<212> TYPE: DNA
<213> ORGANISM: Artificial
<220> FEATURE:
<223> OTHER INFORMATION: Synthetic

<400> SEQUENCE: 114
uaagacgaac aguagguu                                                18

<210> SEQ ID NO 115
<211> LENGTH: 17
<212> TYPE: DNA
<213> ORGANISM: Artificial
<220> FEATURE:
<223> OTHER INFORMATION: Synthetic

<400> SEQUENCE: 115
uaagacgaac aguaggu                                                 17

<210> SEQ ID NO 116
<211> LENGTH: 18
<212> TYPE: DNA
<213> ORGANISM: Artificial
<220> FEATURE:
<223> OTHER INFORMATION: Synthetic

<400> SEQUENCE: 116
aagacgaaca guagguuu                                                18

<210> SEQ ID NO 117
<211> LENGTH: 17
<212> TYPE: DNA
<213> ORGANISM: Artificial
<220> FEATURE:
<223> OTHER INFORMATION: Synthetic

<400> SEQUENCE: 117
aagacgaaca guagguu                                                 17

<210> SEQ ID NO 118
<211> LENGTH: 18
<212> TYPE: DNA
<213> ORGANISM: Artificial
<220> FEATURE:
<223> OTHER INFORMATION: Synthetic

<400> SEQUENCE: 118
agacgaacag uagguuug                                                18
```

```
<210> SEQ ID NO 119
<211> LENGTH: 17
<212> TYPE: DNA
<213> ORGANISM: Artificial
<220> FEATURE:
<223> OTHER INFORMATION: Synthetic

<400> SEQUENCE: 119
agacgaacag uagguuu                                                   17

<210> SEQ ID NO 120
<211> LENGTH: 17
<212> TYPE: DNA
<213> ORGANISM: Artificial
<220> FEATURE:
<223> OTHER INFORMATION: Synthetic

<400> SEQUENCE: 120
gacgaacagu agguuug                                                   17

<210> SEQ ID NO 121
<211> LENGTH: 21
<212> TYPE: DNA
<213> ORGANISM: Artificial
<220> FEATURE:
<223> OTHER INFORMATION: Synthetic

<400> SEQUENCE: 121
uuaagacgaa caaaagguuu g                                              21

<210> SEQ ID NO 122
<211> LENGTH: 20
<212> TYPE: DNA
<213> ORGANISM: Artificial
<220> FEATURE:
<223> OTHER INFORMATION: Synthetic

<400> SEQUENCE: 122
uuaagacgaa caaaagguuu                                                20

<210> SEQ ID NO 123
<211> LENGTH: 19
<212> TYPE: DNA
<213> ORGANISM: Artificial
<220> FEATURE:
<223> OTHER INFORMATION: Synthetic

<400> SEQUENCE: 123
uuaagacgaa caaaagguu                                                 19

<210> SEQ ID NO 124
<211> LENGTH: 18
<212> TYPE: DNA
<213> ORGANISM: Artificial
<220> FEATURE:
<223> OTHER INFORMATION: Synthetic

<400> SEQUENCE: 124
uuaagacgaa caaaaggu                                                  18

<210> SEQ ID NO 125
<211> LENGTH: 17
<212> TYPE: DNA
<213> ORGANISM: Artificial
<220> FEATURE:
<223> OTHER INFORMATION: Synthetic
```

```
<400> SEQUENCE: 125
uuaagacgaa caaaagg                                              17

<210> SEQ ID NO 126
<211> LENGTH: 16
<212> TYPE: DNA
<213> ORGANISM: Artificial
<220> FEATURE:
<223> OTHER INFORMATION: Synthetic

<400> SEQUENCE: 126
uaagacgaac aaaagg                                               16

<210> SEQ ID NO 127
<211> LENGTH: 15
<212> TYPE: DNA
<213> ORGANISM: Artificial
<220> FEATURE:
<223> OTHER INFORMATION: Synthetic

<400> SEQUENCE: 127
aagacgaaca aaagg                                                15

<210> SEQ ID NO 128
<211> LENGTH: 13
<212> TYPE: DNA
<213> ORGANISM: Artificial
<220> FEATURE:
<223> OTHER INFORMATION: Synthetic

<400> SEQUENCE: 128
aagacgaaca aaa                                                  13

<210> SEQ ID NO 129
<211> LENGTH: 12
<212> TYPE: DNA
<213> ORGANISM: Artificial
<220> FEATURE:
<223> OTHER INFORMATION: Synthetic

<400> SEQUENCE: 129
uaagacgaac aa                                                   12

<210> SEQ ID NO 130
<211> LENGTH: 11
<212> TYPE: DNA
<213> ORGANISM: Artificial
<220> FEATURE:
<223> OTHER INFORMATION: Synthetic

<400> SEQUENCE: 130
uaagacgaac a                                                    11

<210> SEQ ID NO 131
<211> LENGTH: 11
<212> TYPE: DNA
<213> ORGANISM: Artificial
<220> FEATURE:
<223> OTHER INFORMATION: Synthetic

<400> SEQUENCE: 131
uaagacuaac a                                                    11

<210> SEQ ID NO 132
```

```
<211> LENGTH: 11
<212> TYPE: DNA
<213> ORGANISM: Artificial
<220> FEATURE:
<223> OTHER INFORMATION: Synthetic

<400> SEQUENCE: 132
uaagacguac a                                                              11

<210> SEQ ID NO 133
<211> LENGTH: 11
<212> TYPE: DNA
<213> ORGANISM: Artificial
<220> FEATURE:
<223> OTHER INFORMATION: Synthetic

<400> SEQUENCE: 133
uaagacgagc a                                                              11

<210> SEQ ID NO 134
<211> LENGTH: 23
<212> TYPE: RNA
<213> ORGANISM: Mus musculus

<400> SEQUENCE: 134
acauacuucu uuauguaccc aua                                                 23

<210> SEQ ID NO 135
<211> LENGTH: 26
<212> TYPE: DNA
<213> ORGANISM: Artificial
<220> FEATURE:
<223> OTHER INFORMATION: Synthetic

<400> SEQUENCE: 135
acauacuucu uuauguagua cccaua                                              26

<210> SEQ ID NO 136
<211> LENGTH: 22
<212> TYPE: DNA
<213> ORGANISM: Artificial
<220> FEATURE:
<223> OTHER INFORMATION: Synthetic

<400> SEQUENCE: 136
auaagacgag caaaaagcuu gu                                                  22

<210> SEQ ID NO 137
<211> LENGTH: 22
<212> TYPE: DNA
<213> ORGANISM: Artificial
<220> FEATURE:
<223> OTHER INFORMATION: Synthetic

<400> SEQUENCE: 137
aagcuuuuug cucgcguuau gu                                                  22

<210> SEQ ID NO 138
<211> LENGTH: 116
<212> TYPE: PRT
<213> ORGANISM: Homo sapiens

<400> SEQUENCE: 138

Ser Pro Lys His His Pro Gln Arg Ser Arg Lys Lys Asn Lys Asn Cys
 1               5                  10                  15
```

-continued

```
Arg Arg His Ser Leu Tyr Val Asp Phe Ser Asp Val Gly Trp Asn Asp
            20              25              30

Trp Ile Val Ala Pro Pro Gly Tyr Gln Ala Phe Tyr Cys His Gly Asp
        35              40              45

Cys Pro Phe Pro Leu Ala Asp His Leu Asn Ser Thr Asn His Ala Ile
    50              55              60

Val Gln Thr Leu Val Asn Ser Val Asn Ser Ser Ile Pro Lys Ala Cys
65              70              75              80

Cys Val Pro Thr Glu Leu Ser Ala Ile Ser Met Leu Tyr Leu Asp Glu
            85              90              95

Tyr Asp Lys Val Val Leu Lys Asn Tyr Gln Glu Met Val Val Glu Gly
            100             105             110

Cys Gly Cys Arg
        115
```